US 9,040,729 B2

(12) United States Patent
Lutz et al.

(10) Patent No.: US 9,040,729 B2
(45) Date of Patent: *May 26, 2015

(54) PROCESSES OF PREPARING ESTOLIDE COMPOUNDS THAT INCLUDE REMOVING SULFONATE RESIDUES

(71) Applicant: BIOSYNTHETIC TECHNOLOGIES, LLC, Irvine, CA (US)

(72) Inventors: Marlon Lutz, Grayslake, IL (US); Igor Likhotvorik, Willmette, IL (US); Chris Arnold, Mount Prospect, IL (US); Travis Thompson, Anaheim, CA (US); Dean Kent Hoglen, Baton Rouge, LA (US); Eric Lee Williams, Zachary, LA (US)

(73) Assignee: Biosynthetic Technologies, LLC, Irvine, CA (US)

( * ) Notice: Subject to any disclaimer, the term of this patent is extended or adjusted under 35 U.S.C. 154(b) by 21 days.

This patent is subject to a terminal disclaimer.

(21) Appl. No.: 14/049,101

(22) Filed: Oct. 8, 2013

(65) Prior Publication Data

US 2014/0039211 A1 Feb. 6, 2014

Related U.S. Application Data

(63) Continuation of application No. 13/787,556, filed on Mar. 6, 2013, now Pat. No. 8,586,771.

(60) Provisional application No. 61/661,010, filed on Jun. 18, 2012.

(51) Int. Cl.
| | | |
|---|---|---|
| C07C 59/235 | (2006.01) | |
| C07C 67/327 | (2006.01) | |
| C11C 3/00 | (2006.01) | |
| C11C 3/08 | (2006.01) | |
| C11C 3/14 | (2006.01) | |

(52) U.S. Cl.
CPC .............. *C07C 67/327* (2013.01); *C11C 3/006* (2013.01); *C11C 3/08* (2013.01); *C11C 3/14* (2013.01)

(58) Field of Classification Search
None
See application file for complete search history.

(56) References Cited

U.S. PATENT DOCUMENTS

| | | | |
|---|---|---|---|
| 2,049,072 A | 7/1936 | Mikeska et al. |
| 2,652,411 A | 9/1953 | Teeter et al. |
| 2,862,884 A | 12/1958 | Dilworth et al. |
| 3,299,110 A | 1/1967 | Pine |
| 4,428,850 A | 1/1984 | Zoleski et al. |
| 4,431,673 A | 2/1984 | Goldner et al. |
| 4,567,037 A | 1/1986 | Ciaudelli |
| 4,639,369 A | 1/1987 | Ciaudelli |
| 4,806,572 A | 2/1989 | Kellett |
| 4,867,965 A | 9/1989 | Ciaudelli |
| 5,011,629 A | 4/1991 | Bilbo |
| 5,021,311 A | 6/1991 | Kato et al. |
| 5,204,375 A | 4/1993 | Kusakawa et al. |
| 5,380,894 A | 1/1995 | Burg et al. |
| 5,427,704 A | 6/1995 | Lawate |
| 5,451,332 A | 9/1995 | Lawate |
| 5,518,728 A | 5/1996 | Burdzy et al. |
| 5,658,863 A | 8/1997 | Duncan et al. |

(Continued)

FOREIGN PATENT DOCUMENTS

| | | |
|---|---|---|
| EP | 0 665 284 A2 | 8/1995 |
| FR | 2906530 A1 | 4/2008 |

(Continued)

OTHER PUBLICATIONS

Aguieiras et al., "Estolide Synthesis Catalyzed by Immobilized Lipases," *Enzyme Research*, ID432746, 1-7 (2011).
Ahmad et al., "Oleochemicals from Isoricinoleic Acid (Wrightia tinctoria Seed Oil)", *Ind. Eng. Chem. Res.*, 47: 2091-2095 (2008).
Bethell et al., "The hydrolysis of $C_{12}$ primary alkyl sulfates in concentrated aqueous solutions. Part 1. General features, kinetic form and mode of catalysis in sodium dodecyl sulfate hydrolysis", *J. Chem. Soc., Perkin Trans. 2*, 1489-1495 (2001).
Burton et al., "The Constitution of Sulphated Oils. V.—Effects of Variations in Preparation on the Composition of Sulphated Oleic Acid." *J. Leather Tech. Chem.*, 37: 321-330 (1953).

(Continued)

*Primary Examiner* — Yate K Cutliff
(74) *Attorney, Agent, or Firm* — Jeremy Forest

(57) ABSTRACT

Provided herein are processes of preparing sulfonated estolide compounds, and the removal of sulfonate residues from those compounds to provide desulfonated estolide base oils. Exemplary sulfonated estolide compounds include those selected from the formula:

$$\begin{array}{c} R_6 \\ | \\ O=S=O \\ | \\ O \\ | \\ CH_3(CH_2)_q CH(CH_2)_z C \\ \end{array} \begin{array}{c} O \\ \| \\ \end{array}$$

$$\left[ CH_3(CH_2)_y CH(CH_2)_x C \begin{array}{c} O \\ \| \\ \end{array} \right]_n$$

$$CH_3(CH_2)_y CH(CH_2)_x C \begin{array}{c} O \\ \| \\ OR_2 \end{array}$$

wherein z is an integer selected from 0 to 15; q is an integer selected from 0 to 15; x is, independently for each occurrence, an integer selected from 0 to 20; y is, independently for each occurrence, an integer selected 0 to 20; n is equal to or greater than 0; $R_6$ is selected from —OH, optionally substituted alkyl, and optionally substituted aryl; and $R_2$ is selected from hydrogen and optionally substituted alkyl that is saturated or unsaturated, and branched or unbranched, wherein each fatty acid chain residue of said compounds is independently optionally substituted.

34 Claims, No Drawings

(56) References Cited

U.S. PATENT DOCUMENTS

| | | | |
|---|---|---|---|
| 6,018,063 | A | 1/2000 | Isbell et al. |
| 6,160,144 | A | 12/2000 | Bongardt et al. |
| 6,316,649 | B1 | 11/2001 | Cermak et al. |
| 7,119,216 | B2 | 10/2006 | Newman et al. |
| 7,252,779 | B2 | 8/2007 | Mosier et al. |
| 7,651,641 | B2 | 1/2010 | Corkran et al. |
| 7,666,828 | B2 | 2/2010 | Bernhardt et al. |
| 7,960,599 | B2 | 6/2011 | Millis et al. |
| 8,115,021 | B2 | 2/2012 | Tupy et al. |
| 8,236,194 | B1 | 8/2012 | Bredsguard et al. |
| 8,258,326 | B1 | 9/2012 | Forest et al. |
| 8,268,199 | B1 | 9/2012 | Forest et al. |
| 8,287,754 | B1 | 10/2012 | Bredsguard et al. |
| 8,372,301 | B2 | 2/2013 | Bredsguard et al. |
| 8,399,389 | B2 | 3/2013 | Bredsguard et al. |
| 8,404,867 | B2 | 3/2013 | Forest et al. |
| 8,512,592 | B2 | 8/2013 | Forest et al. |
| 8,541,351 | B2 | 9/2013 | Thompson et al. |
| 2002/0017629 | A1 | 2/2002 | Mosier et al. |
| 2002/0193262 | A1 | 12/2002 | Kaimai et al. |
| 2004/0046146 | A1 | 3/2004 | Ankner et al. |
| 2007/0092475 | A1 | 4/2007 | Wohlman |
| 2007/0161832 | A1 | 7/2007 | Myllyoja et al. |
| 2008/0020956 | A1 | 1/2008 | Mosier et al. |
| 2009/0012324 | A1 | 1/2009 | Choi et al. |
| 2009/0159835 | A1 | 6/2009 | Kramer et al. |
| 2009/0159837 | A1 | 6/2009 | Kramer et al. |
| 2009/0187042 | A1 | 7/2009 | Ishihara et al. |
| 2010/0120643 | A1 | 5/2010 | Brown et al. |
| 2010/0145086 | A1 | 6/2010 | Schrodi et al. |
| 2010/0184855 | A1 | 7/2010 | Bernhardt et al. |
| 2010/0292328 | A1 | 11/2010 | Althaus et al. |
| 2011/0028747 | A1 | 2/2011 | Cho et al. |
| 2011/0092723 | A1 | 4/2011 | Rosas et al. |
| 2011/0105814 | A1 | 5/2011 | Koivusalmi et al. |
| 2011/0294174 | A1 | 12/2011 | Franklin et al. |
| 2012/0018667 | A1 | 1/2012 | Krammer et al. |
| 2012/0083435 | A1 | 4/2012 | Bredsguard |
| 2012/0136168 | A1 | 5/2012 | Kersbulck et al. |
| 2012/0172269 | A1 | 7/2012 | Greaves et al. |
| 2012/0172609 | A1 | 7/2012 | Bredsguard et al. |
| 2012/0178660 | A1 | 7/2012 | Bredsguard |

FOREIGN PATENT DOCUMENTS

| | | |
|---|---|---|
| JP | 5-150560 | 6/1993 |
| JP | 7228881 | 8/1995 |
| JP | 2002196543 | 7/2002 |
| JP | 2004051789 | 2/2004 |
| WO | WO-99/25794 | 5/1999 |
| WO | WO-01/53247 A1 | 7/2001 |
| WO | WO-03/011455 A1 | 2/2003 |
| WO | WO-2008/040864 A1 | 4/2008 |
| WO | WO-2009/139003 A1 | 11/2009 |
| WO | WO-2011/037778 A1 | 3/2011 |
| WO | WO-2011/106186 A1 | 9/2011 |
| WO | WO-2012/030398 A1 | 3/2012 |
| WO | WO-2012/061101 A1 | 5/2012 |

OTHER PUBLICATIONS

Biresaw et al., "Film-forming properties of estolides," *Tribology Letters*, 27(1): 69-78 (2007).

Brutting et al., "Produkte der Dimerisierung ungesättigter Fettsauren X: Identifizierung von Estoliden in der Anfangsphase der Dimerisierung," *Fat Sci. Technol.*, 95(5): 193-99 (1993).

Budarin et al., "Versatile mesoporous carbonaceous materials for acid catalysis," *Chem. Commun.*, pp. 634-636 (2007).

Cermak et al., "Synthesis and Physical Properties of New Estolide Esters", *Industrial Crops and Products*, 46: 386-391 (2013).

Cermak et al., "Synthesis of Estolides from Oleic and Saturated Fatty Acids," *JAOCS*, 78(6): 557-65 (2001).

Cermak et al., "Physical properties of saturated estolides and their 2-ethylhexyl esters," 16: 119-27 (2002).

Cermak et al., "Synthesis and physical properties of estolide-based functional fluids," *Indus. Crops and Prods.*, 18: 183-96 (2003).

Cermak et al., "Improved oxidative stability of estolide esters," *Indus. Crops and Prods.*, 18: 223-30 (2003).

Cermak et al., "Synthesis and Physical Properties of Cuphea-Oleic Estolides and Esters," *JAOCS*, 81(3): 297-303 (2004).

Cermak et al., "Synthesis and physical properties of estolides from lesquerella and castor fatty acid esters," *Indus. Crops and Prods.*, 23: 256-63 (2006).

Cermak et al., "Synthesis and Physical Properties of Tallow-Oleic Estolide 2-Ethylhexyl Esters," *J. Amer. Oil Chem. Soc.*, 84(5): 449-56 (2007).

Cermak et al., "Comparison of a New Estolide Oxidative Stability Package," *J. Am. Oil Chem. Soc.*, 85: 879-885 (2008).

Cermak et al., "Synthesis and physical properties of mono-estolides with varying chain lengths," *Indus. Crops and Prods.*, 29: 205-13 (2009).

Choi et al., "Iron-catalysed green synthesis of carboxylic esters by the intermolecular addition of carboxylic acids to alkenes," *Chem. Commun.*, pp. 777-779 (2008).

Dobbs et al., "First Total Synthesis of the Irciniasulfonic Acids ", *Synlett.*, 4: 652-654 (2005).

Dorwald, *Side Reactions in Organic Synthesis*, Wiley: VCH, Weinheim p. IX of Preface and pp. 1-15 (2005).

Dunn, "Effect of antioxidants on the oxidative stability of methyl soyate (biodiesel)," *Fuel Process. Tech.*, 86: 1071-1085 (2005).

Erhan et al., "Estolides from Meadowfoam Oil Fatty Acids and Other Monounsaturated Fatty Acids," *JAOCS*, 70:5, 461-465 (May 1993).

Erhan et al., "Estolide Production with Modified Clay Catalysts and Process Conditions," *JAOCS*, 74(3): 249-54 (1997).

Erhan et al., "Biodegradation of Estolides from Monounsaturated Fatty Acids," *JAOCS*, 74(5): 605-07 (1997).

Teeter et al., "Synthetic Lubricants from Hydroxystearic Acids," *Indus. and Eng. Chem.*, 45(8): 1777-79 (1953).

Garcia-Zapateiro et al., "Viscous, thermal and tribological characterization of oleic and ricinoleic acids-derived estolides and their blends with vegetable oils", *Journal of Indus. and Engin. Chem.*, 19: 1289-1298 (2013).

Gast et al., "Synthetic Lubricants from Polyhydroxystearic Acids," *Indus. and Eng. Chem.*, 46(10): 2205-08 (1954).

Goossen et al., "Silver triflate-catalysed synthesis of γ-lactones from fatty acids," *Green Chem.*, 12: 197-200 (2010).

Harry-O'Kuru et al., "Synthesis of Estolide Esters from cis-9-Octadecanoic Acid Estolides," *JAOCS*, 78(3): 219-23 (2001).

Heydarzadeh et al., "Esterification of Free Fatty Acids by Heterogeneous γ-Alumina-Zirconia Catalysts for Biodiesel Synthesis," *World App. Sci. J.*, 9(11): 1306-12 (2010).

Isbell et al., "Acid-Catalyzed Condensation of Oleic Acid into Estolides and Polyestolides," *JAOCS*, 71(2): 169-74 (1994).

Isbell et al., "Characterization of Estolides Produced from Acid-Catalyzed Condensation of Oleic Acid," *JAOCS*, 71(4): 379-83 (1994).

Isbell et al., "Optimization of the Sulfuric Acid-Catalyzed Estolide Synthesis from Oleic Acid," *JAOCS*, 74(4): 473-76 (1997).

Isbell et al., "Physical properties of estolides and their ester derivatives," *Indus. Crops and Prods.*, 13: 11-20 (2001).

Isbell et al., "Physical properties of triglyceride estolides from lesquerella and castor oils," *Indus. Crops and Prods.*, 23: 256-253 (2006).

Ishihara et al., "Direct Condensation of Carboxylic Acids with Alcohols Catalyzed by Hafnium(IV) Salts," *Science*, 290: 1140-42 (2000).

Komura et al., "FeCl3•6H20 as a Versatile Catalyst for the Esterification of Steroid Alcohols with Fatty Acids," *Synthesis*, 21: 3407-10 (2008).

Kulkarni et al., "Kinetics of the Catalytic Esterification of Castor Oil with Lauric Acid Using n-Butyl Benzene as a Water Entrainer," *JAOCS*, 80:10, 1033-1038 (2003).

Kwie et al., "Bismuth (III) Triflate: A Safe and Easily Handled Precursor for Triflic Acid: Application to the Esterification Reaction," *Syn. Comm.*, 40: 1082-1087 (2010).

Lotero et al., "Synthesis of Biodiesel via Acid Catalysis," *Ind. Eng. Chem.*, 44: 5353-5363 (2005).

(56) References Cited

OTHER PUBLICATIONS

Mantri et al., "ZrOCl2•8H2O catalysts for the esterification of long chain aliphatic carboxylic acids and alcohols. The enhancement of catalytic performance by supporting on ordered mesoporous silica," *Green Chem.*, 7: 677-82 (2005).
Mathers et al., "A General Polymerization Method Using Hydoralkoxylation and Hydrocarboxylation Reactions Catalyzed by Triflic Acid," *Macromolecules*, 41, 524-526 (2008).
Nakayama et al., "Water-Tolerant and Reusable Catalysts for Direct Ester Condensation between Equimolar Amounts of Carboxylic Acids and Alcohols," *Adv. Syn. Catal.*, 346: 1275-79 (2004).
Nordin et al., "New Silica Supported HClO4 as Efficient Catalysts for Estolide Synthesis from Oleic Acid," *Adv. Mat. Res.*, 173: 140-45 (2011).
Rudnick, L. R., *Synthetics, Mineral Oils, and Bio-Based Lubricants*, CRC Press, Boca Raton, FL.; Chap. 22, pp. 371-374 (2006).
Sadek, E.M., "Some Study on Esterification of Maleic Acid with 2-Ethyl hexyl Alcohol," *Jour. Chem. Soc. Pak.*, 20(4): 271-75 (1998).
Salimon et al., "Synthesis and Physical Properties of Estolide Ester Using Saturated Fatty Acid and Ricinoleic Acid," *J. Auto. Methods and Manag. Chem.*, ID263624,1-4 (2011).
Socha et al., "Efficient conversion of triacylglycerols and fatty acids to biodiesel in a microwave reactor using metal triflate catalysts," *Org. Biomol. Chem.*, 8: 4753-56 (2010).
Simonsick et al., "Details structural elucidation of polyesters and acrylates using Fourier transform mass spectroscopy," *Anal. Bioanal. Chem.*, 392: 575-583 (2008).
Suwannakarn et al., "Stability of sulfated zirconia and the nature of the catalytically active species in the transesterification of triglycerides," *J. Cat.*, 255: 279-86 (2008).
Takagaki et al., "Esterification of higher fatty acids by a novel strong solid acid," *Catalysis Today*, 116: 157-61 (2006).
Taylor et al., "Copper(II)-catalysed addition of O—H bonds to norbornene," *Chem. Commun.*, pp. 5103-5105 (2005).
Tomoda et al., "Characteristic Properties of Cutting Fluid Additives Derived From the Reaction Products of Hydroxyl Fatty Acids With Some Acid Anhydrides," *J. of Surf. and Deter.*, 1:4, 533-537 (Oct. 1998).
Troast et al., "Studies Towards the Synthesis of (-)-Zampanolide: Preparation of N-Acyl Hemiaminal Model Systems", *Org. Lett.*, 4(6): 991-994 (2002).
Yan et al., "Advancements in Heterogeneous Catalysis for Biodiesel Synthesis," *Top Catal.*, 53: 721-36 (2010).
Zerkowski, J., "Estolides: From structure and function to structured and functionalized," *Lipid Tech.*, 20(11): 253-56 (2008).
Zhou et al., "Solid acid catalysis of tandem isomerization-lactonization of olefinic acids," *App. Cat.*, 333: 238-44 (2007).
Abstract of JP 7228881, published Aug. 29, 1995.
Abstract of JP 5-150560, published Jun. 18, 1993.
Abstract of JP-2002196543, published Jul. 12, 2002.
Abstract of JP-2004051789, published Feb. 19, 2004.
Cann et al., "Polymerization of Undecylenic Acid in the Presence of Boron Fluoride," *J. Am. Chem. Soc.*, 66(5): 839-840 (1944).
Meier et al., "Plant Oil Renewable Resources as Green Alternatives in Polymer Science," *Chem. Soc. Rev.*, 36: 1788-1802 (2007).
Mol et al., "Catalytic Metathesis of Unsaturated Fatty Acid Esters and Oils," *Topics in Catalysis*, 27, Nos. 1-4: 97-104 (2004).
Ross et al., "The Polymerization of Undecylenic Acid," *J. Am. Chem. Soc.*, 67(8): 1275-1278 (1945).
Skupinska et al., "Oligomerization of α-Olefins to Higher Oligomers," *Chem. Rev.*, 91: 613-648 (1991).
International Search Report and Written Opinion mailed Nov. 30, 2011 in international application PCT/US2011/001537.
Written Opinion of the International Searching Authority in international application PCT/US2011/001537, filed Aug. 31, 2011.
International Preliminary Report on Patentability in international application PCT/US2011/001537, mailed Mar. 5, 2013.
International Search Report and Written Opinion mailed Nov. 23, 2011 in international application PCT/US2011/050102.

Written Opinion of the International Searching Authority in international application PCT/US2011/050102, filed Aug. 31, 2011.
International Preliminary Report on Patentability in international application PCT/US2011/050102, mailed Mar. 5, 2013.
International Search Report and Written Opinion mailed Nov. 23, 2011 in international application No. PCT/US2011/001540.
Article 19 Amendments and Letter Accompanying Replacement Sheets in international application PCT/US2011/001540, filed Jan. 28, 2012.
Reply to Written Opinion for counterpart application PCT/US2011/001540, filed Jun. 28, 2012.
Written Opinion of the International Preliminary Examining Authority for international application PCT/US2011/001540, filed Jun. 28, 2012.
International Preliminary Report on Patentability in international application PCT/US2011/001540, mailed Nov. 15, 2012.
International Search Report and Written Opinion mailed Apr. 11, 2012 in international application PCT/US2012/023933.
International Search Report and Written Opinion mailed May 15, 2012 in international application PCT/US2012/026887.
International Search Report and Written Opinion mailed Apr. 26, 2012 in international application PCT/US2012/024260.
International Search Report and Written Opinion in international application PCT/US2012/026538, mailed Apr. 26, 2012.
Article 19 Amendments and Letter Accompanying Replacement Sheets in international application PCT/US2012/026538, filed May 17, 2012.
Informal Comments filed in response to International Search Report and Written Opinion for international application PCT/US2012/026538, filed May 17, 2012.
International Search Report and Written Opinion in international application PCT/US2012/039937, mailed Aug. 6, 2012.
International Search Report and Written Opinion in international application PCT/US2012/053316 mailed Nov. 2, 2012.
International Search Report and Written Opinion for international application PCT/US12/68293 mailed Apr. 24, 2013.
International Search Report and Written Opinion for international application PCT/US2013/029426 mailed Jun. 6, 2013.
Co-Pending U.S. Appl. No. 13/199,554, filed Aug. 31, 2011.
Office Action dated Jul. 3, 2012, for U.S. Appl. No. 13/199,554, filed Aug. 31, 2011.
Office Action dated Nov. 2, 2012, for U.S. Appl. No. 13/199,554, filed Aug. 31, 2011.
Office Action dated Nov. 16, 2012, for U.S. Appl. No. 13/199,554, filed Aug. 31, 2011.
Notice of Allowance dated Jan. 4, 2013, for U.S. Appl. No. 13/199,554, filed Aug. 31, 2011.
Co-Pending U.S. Appl. No. 13/711,388, filed Dec. 11, 2012.
Office Action dated Mar. 25, 2013, for U.S. Appl. No. 13/711,388, filed Dec. 11, 2012.
Notice of Allowance dated Apr. 22, 2013, for U.S. Appl. No. 13/711,388, filed Dec. 11, 2012.
Co-Pending U.S. Appl. No. 13/865,495, filed Apr. 18, 2013.
Co-Pending U.S. Appl. No. 13/223,008, filed Aug. 31, 2011.
Office Action dated Jan. 17, 2013, for U.S. Appl. No. 13/223,008, filed Aug. 31, 2011.
Notice of Allowance dated Apr. 15, 2013, for U.S. Appl. No. 13/223,008, filed Aug. 31, 2011.
Co-Pending U.S. Appl. No. 13/865,520, filed Apr. 18, 2013.
Co-Pending U.S. Appl. No. 13/199,551, filed Aug. 31, 2011.
Office Action dated Sep. 9, 2013, for U.S. Appl. No. 13/199,551, filed Aug. 31, 2011.
Co-Pending U.S. Appl. No. 13/366,667, filed Feb. 2, 2012.
Co-Pending U.S. Appl. No. 13/936,015, filed Jul. 5, 2013.
Co-Pending U.S. Appl. No. 13/766,138, filed Feb. 13, 2013.
Co-Pending U.S. Appl. No. 13/754,775, filed Jan. 30, 2013.
Co-Pending U.S. Appl. No. 13/950,508, filed Jul. 25, 2013.
Co-Pending U.S. Appl. No. 13/534,424, filed Jun. 27, 2012.
Co-Pending U.S. Appl. No. 13/600,704, filed Aug. 31, 2012.
Co-Pending U.S. Appl. No. 13/707,480, filed Dec. 6, 2012.

(56) References Cited

OTHER PUBLICATIONS

Office Action dated Feb. 28, 2013, for U.S. Appl. No. 13/707,480, filed Dec. 6, 2012.
Office Action dated Jun. 5, 2013, for U.S. Appl. No. 13/707,480, filed Dec. 6, 2012.
Office Action dated Aug. 30, 2013, for U.S. Appl. No. 13/707,480, filed Dec. 6, 2012.
Notice of Allowance dated Sep. 20, 2013, for U.S. Appl. No. 13/707,480, filed Dec. 6, 2012.
Co-Pending U.S. Appl. No. 14/026,387, filed Sep. 13, 2013.
Co-Pending U.S. Appl. No. 13/787,556, filed Mar. 6, 2013.
Office Action dated Jul. 15, 2013, for U.S. Appl. No. 13/787,556, filed Mar. 6, 2013.
Notice of Allowance dated Sep. 23, 2013, for U.S. Appl. No. 13/787,480, filed Mar. 6, 2013.
Co-Pending U.S. Appl. No. 13/875,172, filed May 1, 2013.

PROCESSES OF PREPARING ESTOLIDE COMPOUNDS THAT INCLUDE REMOVING SULFONATE RESIDUES

CROSS-REFERENCE TO RELATED APPLICATIONS

This application is a continuation of U.S. application Ser. No. 13/787,556, filed Mar. 6, 2013, which claims the benefit under 35 U.S.C. §119(e) of U.S. Provisional Patent Application No. 61/661,010, filed Jun. 18, 2012, which is incorporated herein by reference in its entirety for all purposes.

FIELD

The present disclosure relates to sulfonated estolide compounds and methods of making the same, as well as processes of preparing estolide base oils that include the removal of sulfonate residues.

BACKGROUND

Lubricant compositions typically comprise a base oil, such as a hydrocarbon base oil, and one or more additives. Estolides present a potential source of biobased, biodegradable oils that may be useful as lubricants and base stocks.

SUMMARY

Described herein are estolide compounds, estolide-containing compositions, and methods of making the same. In certain embodiments, such compounds and/or compositions may be useful as lubricants and additives. In certain embodiments, the estolide compounds are prepared by a process wherein said compounds comprise one or more sulfonate residues covalently bound thereto. In certain embodiments, the one or more sulfonate residues are removed from the estolide compounds to provide a desulfonated estolide base oil.

In certain embodiments, the estolides comprise at least one compound of Formula I:

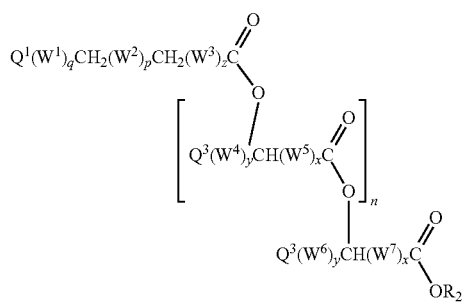

Formula I wherein $W^1$, $W^2$, $W^3$, $W^4$, $W^5$, $W^6$, and $W^7$, independently for each occurrence, are selected from —$CH_2$—, —CH=CH—, and —$CHR_5$—;

$Q^1$, $Q^2$, and $Q^3$, independently for each occurrence, are selected from —$CH_3$, —CH=$CH_2$, —CH($R_5$)$CH_3$, and —$CH_2R_5$, provided that at least one of $W^1$, $W^2$, $W^3$, $W^4$, $W^5$, $W^6$, or $W^7$ is —$CHR_5$—, or at least one of $Q^1$, $Q^2$, or $Q^3$ is —$CH_2R_5$;

$R_5$, independently for each occurrence, is selected from —OS(O)$_2R_6$, wherein $R_6$ is selected from —OH, optionally substituted alkyl, and optionally substituted aryl;

z is an integer selected from 0 to 15;

p is an integer selected from 0 to 15;

q is an integer selected from 0 to 15;

x is, independently for each occurrence, an integer selected from 0 to 20;

y is, independently for each occurrence, an integer selected from 0 to 20;

n is equal to or greater than 0; and $R_2$ is selected from hydrogen and optionally substituted alkyl that is saturated or unsaturated, and branched or unbranched, wherein each fatty acid chain residue of said at least one compound is independently optionally substituted.

In certain embodiments, the estolides comprise at least one compound of Formula II:

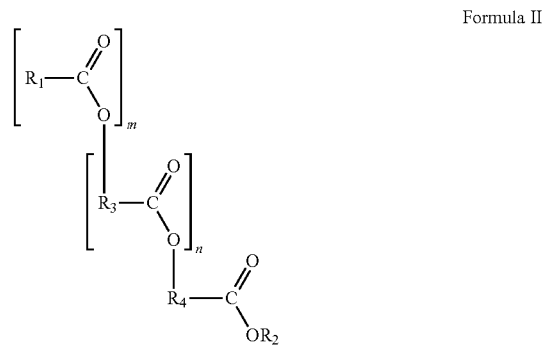

Formula II wherein m is an integer equal to or greater than 1;

n is an integer equal to or greater than 0;

$R_1$, independently for each occurrence, is an optionally substituted alkyl that is saturated or unsaturated, branched or unbranched;

$R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched, wherein at least one of $R_1$, $R_2$, $R_3$, or $R_4$ is substituted with one or more of a sulfate residue, an alkyl sulfonate residue, or an aryl sulfonate residue.

In certain embodiments, the estolides comprise at least one compound of Formula III:

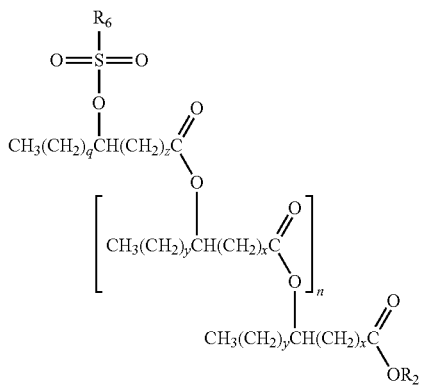

Formula III wherein z is an integer selected from 0, 1, 2, 3, 4, 5, 6, 7, 8, 9, 10, 11, 12, 13, 14, and 15;

q is an integer selected from 0, 1, 2, 3, 4, 5, 6, 7, 8, 9, 10, 11, 12, 13, 14, and 15;

x is, independently for each occurrence, an integer selected from 0, 1, 2, 3, 4, 5, 6, 7, 8, 9, 10, 11, 12, 13, 14, 15, 16, 17, 18, 19, and 20;

y is, independently for each occurrence, an integer selected from 0, 1, 2, 3, 4, 5, 6, 7, 8, 9, 10, 11, 12, 13, 14, 15, 16, 17, 18, 19, and 20;

n is equal to or greater than 0;

$R_6$ is selected from —OH, optionally substituted alkyl, and optionally substituted aryl; and $R_2$ is selected from hydrogen and optionally substituted alkyl that is saturated or unsaturated, and branched or unbranched, wherein each fatty acid chain residue of said at least one compound is independently optionally substituted.

A process of producing a sulfonated estolide is also described. In certain embodiments, the process comprises:

oligomerizing at least one first fatty acid reactant with at least one second fatty acid reactant in the presence of a sulfonic acid catalyst.

A process of producing estolide compounds is also described. In certain embodiments, the process comprises:

providing at least one first estolide compound having at least one sulfonate residue; and removing the at least one sulfonate residue to provide an estolide base oil.

DETAILED DESCRIPTION

The use of lubricants and lubricant-containing compositions may result in the dispersion of such fluids, compounds, and/or compositions in the environment. Petroleum base oils used in common lubricant compositions, as well as additives, are typically non-biodegradable and can be toxic. The present disclosure provides for the preparation and use of compositions comprising partially or fully biodegradable base oils, including base oils comprising one or more estolides.

In certain embodiments, the compositions comprising one or more estolides are partially or fully biodegradable and thereby pose diminished risk to the environment. In certain embodiments, the compositions meet guidelines set for by the Organization for Economic Cooperation and Development (OECD) for degradation and accumulation testing. The OECD has indicated that several tests may be used to determine the "ready biodegradability" of organic chemicals. Aerobic ready biodegradability by OECD 301D measures the mineralization of the test sample to $CO_2$ in closed aerobic microcosms that simulate an aerobic aquatic environment, with microorganisms seeded from a waste-water treatment plant. OECD 301D is considered representative of most aerobic environments that are likely to receive waste materials. Aerobic "ultimate biodegradability" can be determined by OECD 302D. Under OECD 302D, microorganisms are pre-acclimated to biodegradation of the test material during a pre-incubation period, then incubated in sealed vessels with relatively high concentrations of microorganisms and enriched mineral salts medium. OECD 302D ultimately determines whether the test materials are completely biodegradable, albeit under less stringent conditions than "ready biodegradability" assays.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —C(O)NH$_2$ is attached through the carbon atom.

"Alkoxy" by itself or as part of another substituent refers to a radical —OR$^{31}$ where R$^{31}$ is alkyl, cycloalkyl, cycloalkylalkyl, aryl, or arylalkyl, which can be substituted, as defined herein. In some embodiments, alkoxy groups have from 1 to 8 carbon atoms. In some embodiments, alkoxy groups have 1, 2, 3, 4, 5, 6, 7, or 8 carbon atoms. Examples of alkoxy groups include, but are not limited to, methoxy, ethoxy, propoxy, butoxy, cyclohexyloxy, and the like.

"Alkyl" by itself or as part of another substituent refers to a saturated or unsaturated, branched, or straight-chain monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl(allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

Unless otherwise indicated, the term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group comprises from 1 to 40 carbon atoms, in certain embodiments, from 1 to 22 or 1 to 18 carbon atoms, in certain embodiments, from 1 to 16 or 1 to 8 carbon atoms, and in certain embodiments from 1 to 6 or 1 to 3 carbon atoms. In certain embodiments, an alkyl group comprises from 8 to 22 carbon atoms, in certain embodiments, from 8 to 18 or 8 to 16. In some embodiments, the alkyl group comprises from 3 to 20 or 7 to 17 carbons. In some embodiments, the alkyl group comprises 1, 2, 3, 4, 5, 6, 7, 8, 9, 10, 11, 12, 13, 14, 15, 16, 17, 18, 19, 20, 21, or 22 carbon atoms.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered non-aromatic heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can comprise from 5 to 20 carbon atoms, and in certain embodiments, from 5 to 12 carbon atoms. In certain embodiments, an aryl group can comprise 5, 6, 7, 8, 9, 10, 11, 12, 13, 14, 15, 16, 17, 18, 19, or 20 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein.

"Arylalkyl" by itself or as part of another substituent refers to an acyclic alkyl radical in which one of the hydrogen atoms bonded to a carbon atom, typically a terminal or $sp^a$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl, or alkynyl moiety of the arylalkyl group is $C_{1-10}$ and the aryl moiety is $C_{6-20}$, and in certain embodiments, an arylalkyl group is $C_{7-20}$ arylalkyl, e.g., the alkanyl, alkenyl, or alkynyl moiety of the arylalkyl group is $C_{1-8}$ and the aryl moiety is $C_{6-12}$.

Estolide "base oil" and "base stock", unless otherwise indicated, refer to any composition comprising one or more estolide compounds. It should be understood that an estolide "base oil" or "base stock" is not limited to compositions for a particular use, and may generally refer to compositions comprising one or more estolides, including mixtures of estolides. Estolide base oils and base stocks can also include compounds other than estolides.

"Compounds" refers to compounds encompassed by structural Formula I, II, and III herein and includes any specific compounds within the formula whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

For the purposes of the present disclosure, "chiral compounds" are compounds having at least one center of chirality (i.e. at least one asymmetric atom, in particular at least one asymmetric C atom), having an axis of chirality, a plane of chirality or a screw structure. "Achiral compounds" are compounds which are not chiral.

Compounds of Formula I, II, and III include, but are not limited to, optical isomers of compounds of Formula I, II, and III, racemates thereof, and other mixtures thereof. In such embodiments, the single enantiomers or diastereomers, i.e., optically active forms, can be obtained by asymmetric synthesis or by resolution of the racemates. Resolution of the racemates may be accomplished by, for example, chromatography, using, for example a chiral high-pressure liquid chromatography (HPLC) column. However, unless otherwise stated, it should be assumed that Formula I, II, and III cover all asymmetric variants of the compounds described herein, including isomers, racemates, enantiomers, diastereomers, and other mixtures thereof. In addition, compounds of Formula I, II and III include Z- and E-forms (e.g., cis- and trans-forms) of compounds with double bonds. The compounds of Formula I, II, and III may also exist in several tautomeric forms including the enol form, the keto form, and mixtures thereof. Accordingly, the chemical structures depicted herein encompass all possible tautomeric forms of the illustrated compounds.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, and in certain embodiments, $C_{3-12}$ cycloalkyl or $C_{5-12}$ cycloalkyl. In certain embodiments, a cycloalkyl group is a $C_5, C_6, C_7, C_8, C_9, C_{10}, C_{11}, C_{12}, C_{13}, C_{14}$, or $C_{15}$ cycloalkyl.

"Cycloalkylalkyl" by itself or as part of another substituent refers to an acyclic alkyl radical in which one of the hydrogen atoms bonded to a carbon atom, typically a terminal or $sp^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{7-30}$ cycloalkylalkyl, e.g., the alkanyl, alkenyl, or alkynyl moiety of the cycloalkylalkyl group is $C_{1-10}$ and the cycloalkyl moiety is $C_{6-20}$, and in certain embodiments, a cycloalkylalkyl group is $C_{7-20}$ cycloalkylalkyl, e.g., the alkanyl, alkenyl, or alkynyl moiety of the cycloalkylalkyl group is $C_{1-8}$ and the cycloalkyl moiety is $C_{4-20}$ or $C_{6-12}$.

"Halogen" refers to a fluoro, chloro, bromo, or iodo group.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one aromatic ring fused to at least one other ring, which can be aromatic or non-aromatic in which at least one ring atom is a heteroatom. Heteroaryl encompasses 5- to 12-membered aromatic, such as 5- to 7-membered, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, and in certain embodiments from 5- to 12-membered heteroaryl or from 5- to 10-membered heteroaryl. In certain embodiments, a heteroaryl group is a 5-, 6-, 7-, 8-, 9-, 10-, 11-, 12-, 13-, 14-, 15-, 16-, 17-, 18-, 19-, or 20-membered heteroaryl. In certain embodiments heteroaryl groups are those derived from thiophene, pyrrole, benzothiophene, benzofuran, indole, pyridine, quinoline, imidazole, oxazole, and pyrazine.

"Heteroarylalkyl" by itself or as part of another substituent refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, or heteroarylalkynyl is used. In certain embodiments, a heteroarylalkyl group is a 6- to 30-membered heteroarylalkyl, e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Heterocycloalkyl" by itself or as part of another substituent refers to a partially saturated or unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S, Si, etc. Where a specific level of saturation is intended, the nomenclature "heterocycloalkanyl" or "heterocycloalkenyl" is used. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like.

"Heterocycloalkylalkyl" by itself or as part of another substituent refers to an acyclic alkyl radical in which one of the hydrogen atoms bonded to a carbon atom, typically a terminal or $sp^3$ carbon atom, is replaced with a heterocycloalkyl group. Where specific alkyl moieties are intended, the nomenclature heterocycloalkylalkanyl, heterocycloalkylalkenyl, or heterocycloalkylalkynyl is used. In certain embodiments, a heterocycloalkylalkyl group is a 6- to 30-membered heterocycloalkylalkyl, e.g., the alkanyl, alkenyl, or alkynyl moiety of the heterocycloalkylalkyl is 1- to 10-membered and the heterocycloalkyl moiety is a 5- to 20-membered heterocycloalkyl, and in certain embodiments, 6- to 20-membered heterocycloalkylalkyl, e.g., the alkanyl, alkenyl, or alkynyl moiety of the heterocycloalkylalkyl is 1- to 8-membered and the heterocycloalkyl moiety is a 5- to 12-membered heterocycloalkyl.

"Mixture" refers to a collection of molecules or chemical substances. Each component in a mixture can be independently varied. A mixture may contain, or consist essentially of, two or more substances intermingled with or without a constant percentage composition, wherein each component may or may not retain its essential original properties, and where molecular phase mixing may or may not occur. In mixtures, the components making up the mixture may or may not remain distinguishable from each other by virtue of their chemical structure.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Substituted" refers to a group in which one or more hydrogen atoms are independently replaced with the same or different substituent(s). Examples of substituents include, but are not limited to, —$R^{64}$, —$R^{60}$, —$O^-$, —OH, =O, —$OR^{60}$, —$SR^{60}$, —$S^-$, =S, —$NR^{60}R^{61}$, =$NR^{60}$, —CN, —$CF_3$, —OCN, —SCN, —NO, —$NO_2$, =$N_2$, —$N_3$, —$S(O)_2O^-$, —$S(O)_2OH$, —$S(O)_2R^{60}$, —$OS(O_2)O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$, —$C(NR^{62})NR^{60}R^{61}$, —$S(O)_2$, $NR^{60}R^{61}$, —$NR^{63}S(O)_2R^{60}$, —$NR^{63}C(O)R^{60}$, and —$S(O)R^{60}$;

wherein each —$R^{64}$ is independently a halogen; each $R^{60}$ and $R^{61}$ are independently alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or $R^{60}$ and $R^{61}$ together with the nitrogen atom to which they are bonded form a heterocycloalkyl, substituted heterocycloalkyl, heteroaryl, or substituted heteroaryl ring, and $R^{62}$ and $R^{63}$ are independently alkyl, substituted alkyl, aryl, substituted aryl, arylalkyl, substituted arylalkyl, cycloalkyl, substituted cycloalkyl, heterocycloalkyl, substituted heterocycloalkyl, heteroaryl, substituted heteroaryl, heteroarylalkyl, or substituted heteroarylalkyl, or $R^{62}$ and $R^{63}$ together with the atom to which they are bonded form one or more heterocycloalkyl, substituted heterocycloalkyl, heteroaryl, or substituted heteroaryl rings;

wherein the "substituted" substituents, as defined above for $R^{60}$, $R^{61}$, $R^{62}$, and $R^{63}$, are substituted with one or more, such as one, two, or three, groups independently selected from alkyl, -alkyl-OH, —O-haloalkyl, -alkyl-$NH_2$, alkoxy, cycloalkyl, cycloalkylalkyl, heterocycloalkyl, heterocycloalkylalkyl, aryl, heteroaryl, arylalkyl, heteroarylalkyl, —$O^-$, —OH, =O, —O-alkyl, —O-aryl, —O-heteroarylalkyl, —O-cycloalkyl, —O-heterocycloalkyl, —SH, —$S^-$, =S, —S-alkyl, —S-aryl, —S-heteroarylalkyl, —S-cycloalkyl, —S-heterocycloalkyl, —$NH_2$, =NH, —CN, —$CF_3$, —OCN, —SCN, —NO, —$NO_2$, =$N_2$, —$N_3$, —$S(O)_2$ $O^-$, —$S(O)_2$, —$S(O)_2OH$, —$OS(O_2)O^-$, —$SO_2$(alkyl), —$SO_2$(phenyl), —$SO_2$(haloalkyl), —$SO_2NH_2$, —$SO_2NH$(alkyl), —$SO_2NH$(phenyl), —$P(O)(O^-)_2$, —$P(O)(O$-alkyl$)(O^-)$, —$OP(O)(O$-alkyl$)(O$-alkyl$)$, —$CO_2H$, —$C(O)O$(alkyl), —CON(alkyl)(alkyl), —CONH(alkyl), —$CONH_2$, —C(O)(alkyl), —C(O)(phenyl), —C(O)(haloalkyl), —OC(O)(alkyl), —N(alkyl)(alkyl), —NH(alkyl), —N(alkyl)(alkylphenyl), —NH(alkylphenyl), —NHC(O)(alkyl), —NHC(O)(phenyl), —N(alkyl)C(O)(alkyl), and —N(alkyl)C(O)(phenyl).

As used in this specification and the appended claims, the articles "a," "an," and "the" include plural referents unless expressly and unequivocally limited to one referent.

The term "fatty acid" refers to any natural or synthetic carboxylic acid comprising an alkyl chain that may be saturated, monounsaturated, or polyunsaturated, and may have straight or branched chains. The fatty acid may also be substituted. "Fatty acid," as used herein, includes short chain alkyl carboxylic acid including, for example, acetic acid, propionic acid, etc.

The term "fatty acid reactant" refers to any compound or composition comprising a fatty acid residue that is capable of undergoing oligomerization with another fatty acid or fatty acid reactant. As used herein, the term "oligomerization" refers to a process that includes covalent bond formation between two or more monomeric units, e.g., two or more free fatty acids. For example, in certain embodiments, the fatty acid reactant may comprise a saturated or unsaturated fatty acid or fatty acid oligomer. In certain embodiments, a fatty acid oligomer may comprise a first fatty acid that has previously undergone oligomerization with one or more second fatty acids to form an estolide, such as an estolide having a low EN (e.g., dimer). In certain embodiments, the fatty acid reactant may comprise a fatty acid ester, such as an alkyl ester of a monounsaturated fatty acid (e.g., 2-ethylhexyl oleate). It is understood that a "first" fatty acid reactant can comprise the same structure as a "second" fatty acid reactant. For example, in certain embodiments, a reaction mixture may only comprise oleic acid, wherein the first fatty acid reactant and second fatty acid reactant are both oleic acid.

As used herein, the terms "sulfonate" and "sulfonated" generally refer to compounds comprising one or more esters of a sulfonic acid. For example, a "sulfonated estolide" contains a sulfonic ester residue having the general formula —$OS(O)_2R_6$, wherein $R_6$ is an optionally substituted substituent as defined herein. Unless otherwise indicated, a "sulfonate" or "sulfonated" compound will also include one or more esters of sulfuric acid, e.g., sulfates having the general formula —$OS(O)_2OH$. Unless otherwise indicated, the terms "sulfonate" and "sulfonated" as used herein do not include compounds having residues of the general formula —$SO_3X$, wherein X is hydrogen, or a metal or ammonium-type cation.

All numerical ranges herein include all numerical values and ranges of all numerical values within the recited range of numerical values.

The present disclosure relates to estolide compounds, compositions and methods of making the same. In certain embodiments, the present disclosure also relates to estolide compounds, compositions comprising estolide compounds, the synthesis of such compounds, and the formulation of such compositions. In certain embodiments, the present disclosure relates to biosynthetic estolides having desired viscometric properties, while retaining or even improving other properties such as oxidative stability and pour point. In certain embodiments, new methods of preparing estolide compounds exhibiting such properties are provided. The present disclosure also relates to compositions comprising certain estolide compounds exhibiting such properties.

In certain embodiments, the estolides comprise at least one compound of Formula I:

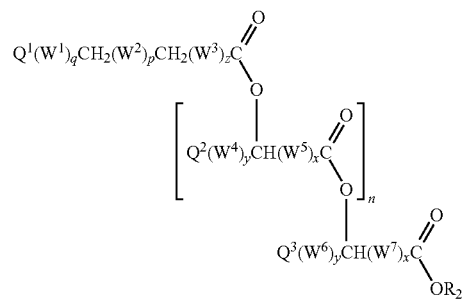

Formula I wherein $W^1$, $W^2$, $W^3$, $W^4$, $W^5$, $W^6$, and $W^7$, independently for each occurrence, are selected from —$CH_2$—, —CH=CH—, and —$CHR_5$—;

$Q^1$, $Q^2$, and $Q^3$, independently for each occurrence, are selected from —$CH_3$, —CH=$CH_2$, —CH($R_5$)$CH_3$, and —$CH_2R_5$, provided that at least one of $W^1$, $W^2$, $W^3$, $W^4$, $W^5$, $W^6$, or $W^7$ is —$CHR_5$—, or at least one of $Q^1$, $Q^2$, or $Q^3$ is —$CH_2R_5$;

$R_5$, independently for each occurrence, is selected from —$OS(O)_2R_6$, wherein $R_6$ is selected from —OH, optionally substituted alkyl, and optionally substituted aryl;

z is an integer selected from 0 to 15;

p is an integer selected from 0 to 15;

q is an integer selected from 0 to 15;

x is, independently for each occurrence, an integer selected from 0 to 20;

y is, independently for each occurrence, an integer selected from 0 to 20;

n is equal to or greater than 0; and $R_2$ is selected from hydrogen and optionally substituted alkyl that is saturated or unsaturated, and branched or unbranched, wherein each fatty acid chain residue of said at least one compound is independently optionally substituted.

In certain embodiments, the estolides comprise at least one compound of Formula II:

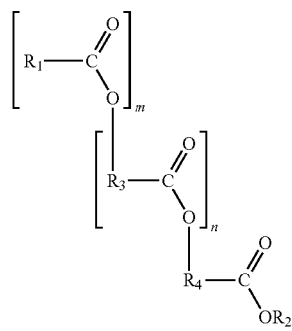

Formula II wherein m is an integer equal to or greater than 1;

n is an integer equal to or greater than 0;

$R_1$, independently for each occurrence, is an optionally substituted alkyl that is saturated or unsaturated, branched or unbranched;

$R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched, wherein at least one of $R_1$, $R_3$, or $R_4$ is substituted with one or more of a sulfate residue, an alkyl sulfonate residue, or an aryl sulfonate residue.

In certain embodiments, the estolides comprise at least one estolide compound of Formula III:

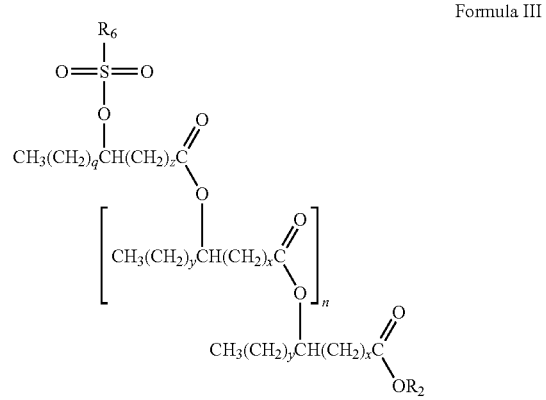

Formula III wherein z is an integer selected from 0, 1, 2, 3, 4, 5, 6, 7, 8, 9, 10, 11, 12, 13, 14, and 15;

q is an integer selected from 0, 1, 2, 3, 4, 5, 6, 7, 8, 9, 10, 11, 12, 13, 14, and 15;

x is, independently for each occurrence, an integer selected from 0, 1, 2, 3, 4, 5, 6, 7, 8, 9, 10, 11, 12, 13, 14, 15, 16, 17, 18, 19, and 20;

y is, independently for each occurrence, an integer selected from 0, 1, 2, 3, 4, 5, 6, 7, 8, 9, 10, 11, 12, 13, 14, 15, 16, 17, 18, 19, and 20;

n is equal to or greater than 0;

$R_6$ is selected from —OH, optionally substituted alkyl, and optionally substituted aryl; and $R_2$ is selected from hydrogen and optionally substituted alkyl that is saturated or unsaturated, and branched or unbranched, wherein each fatty acid chain residue of said at least one compound is independently optionally substituted.

A process of producing a sulfonated estolide is also described. In certain embodiments, the process comprises:

oligomerizing at least one first fatty acid reactant with at least one second fatty acid reactant in the presence of a sulfonic acid catalyst.

In certain embodiments, a process of preparing estolide compounds comprises:

providing at least one first estolide compound having at least one sulfonate residue; and removing the at least one sulfonate residue to provide an estolide base oil.

In certain embodiments, the resulting estolide base oil comprises at least one estolide compound selected from compounds of Formula IV:

Formula IV

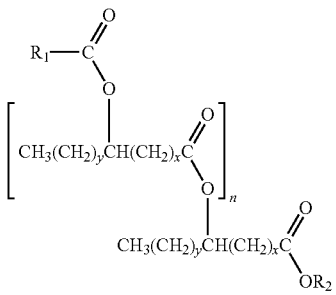

wherein x is, independently for each occurrence, an integer selected from 0, 1, 2, 3, 4, 5, 6, 7, 8, 9, 10, 11, 12, 13, 14, 15, 16, 17, 18, 19, and 20;

y is, independently for each occurrence, an integer selected from 0, 1, 2, 3, 4, 5, 6, 7, 8, 9, 10, 11, 12, 13, 14, 15, 16, 17, 18, 19, and 20;

n is an integer selected from 0, 1, 2, 3, 4, 5, 6, 7, 8, 9, 10, 11, and 12;

$R_1$ is an optionally substituted alkyl that is saturated or unsaturated, and branched or unbranched; and $R_2$ is selected from hydrogen and optionally substituted alkyl that is saturated or unsaturated, and branched or unbranched;

wherein each fatty acid chain residue of said at least one compound is independently optionally substituted.

In certain embodiments, $R_1$ is an alkyl group optionally substituted with a substituent that is not a sulfonate.

The terms "chain" or "fatty acid chain" or "fatty acid chain residue," as used with respect to the estolide compounds of Formula I, II, and III refer to one or more of the fatty acid residues incorporated in estolide compounds, e.g., $R_3$ or $R_4$ of Formula II, the structures represented by

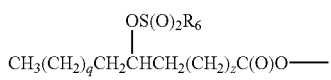

and $CH_3(CH_2)_yCH(CH_2)_xC(O)O-$ in Formula III, or the structures represented by $Q^1(W^1)_qCH_2(W^2)_pCH_2(W^3)_z-C(O)-O-$, $Q^2(W^4)_yCH_2(W^5)-C(O)-O-$, and $Q^3(W^6)_yCH_2(W^7)_x-C(O)-O-$ in Formula I.

The $R_1$ of Formula II or IV is an example of what may be referred to as a "cap" or "capping material," as it "caps" the top of the estolide. For example, the capping group may be an organic acid residue of general formula $Q^1(W^1)_qCH_2(W^2)_pCH_2(W^3)_z-C(O)-O-$, i.e., as reflected in Formula I. In certain embodiments, the "cap" or "capping group" is a fatty acid. In certain embodiments, the capping group, regardless of size, is substituted or unsubstituted, saturated or unsaturated, and/or branched or unbranched. For example, in certain embodiments, the cap is sulfonated, and is thus substituted with at least one alkyl sulfonate residue and/or an aryl sulfonate residue. The cap or capping material may also be referred to as the primary or alpha (α) chain.

Depending on the manner in which the estolide is synthesized, the cap or capping group alkyl may be the only alkyl from an organic acid residue in the resulting estolide that is unsaturated. In certain embodiments, it may be desirable to use a saturated organic or fatty-acid cap to increase the overall saturation of the estolide and/or to increase the resulting estolide's stability. For example, in certain embodiments, it may be desirable to provide a method of providing a saturated capped estolide by hydrogenating an unsaturated cap using any suitable methods available to those of ordinary skill in the art. Hydrogenation may be used with various sources of the fatty-acid feedstock, which may include mono- and/or polyunsaturated fatty acids. Without being bound to any particular theory, in certain embodiments, hydrogenating the estolide may help to improve the overall stability of the molecule. However, a fully-hydrogenated estolide, such as an estolide with a larger fatty acid cap, may exhibit increased pour point temperatures. In certain embodiments, it may be desirable to offset any loss in desirable pour-point characteristics by using shorter, saturated capping materials.

In certain embodiments, the sulfonated estolide will be exposed to conditions that allow for the removal of one or more bound sulfonate residues. In certain embodiments, the sulfonate residue (e.g., mesylate) will be eliminated from the estolide, resulting in an unsaturated estolide base oil and the sulfonic acid (e.g., methanesulfonic acid). In certain embodiments, the sulfonated estolide may be esterified with an alcohol to provide an esterified estolide base oil having at least one sulfonate substituent. In certain embodiments, the sulfonate residue may be removed from the esterified estolide base oil to provide a desulfonated esterified estolide base oil. As noted above, in certain embodiments, it may be desirable to hydrogenate the resulting estolide base oil to provide a saturated product. Accordingly, in certain embodiments, the method of preparing the estolide base oil further comprises hydrogenating the unsaturated estolide intermediate.

The $R_4C(O)O-$ of Formula II, the structure $Q^3(W^6)_yCH(W^7)-C(O)O-$ of Formula I, or the structure $CH_3(CH_2)_yCH(CH_2)_xC(O)O-$ of Formula III serve as the "base" or "base chain residue" of the estolide. Depending on the manner in which the estolide is synthesized, the base organic acid or fatty acid residue may be the only residue that remains in its free-acid form after the initial synthesis of the estolide. However, in certain embodiments, in an effort to alter or improve the properties of the estolide, the free acid may be reacted with any number of substituents. For example, it may be desirable to react the free acid estolide with alcohols, glycols, amines, or other suitable reactants to provide the corresponding ester, amide, or other reaction products. The base or base chain residue may also be referred to as tertiary or gamma (γ) chains.

The $R_3C(O)O-$ of Formula II, $CH_3(CH_2)_yCH(CH_2)_xC(O)O-$ of Formula III, and $Q^2(W^4)_yCH(W^5)_xC(O)O-$ of Formula I are linking residues that link the capping material and the base fatty-acid residue together. There may be any number of linking residues in the estolide, including when n=0 and the estolide is in its dimer form. Depending on the manner in which the estolide is prepared, a linking residue may be a fatty acid and may initially be in an unsaturated form during synthesis. In some embodiments, the estolide will be formed when a catalyst is used to produce a carbocation at the fatty acid's site of unsaturation, which is followed by nucleophilic attack on the carbocation by the carboxylic group of another fatty acid. In some embodiments, it may be desirable to have a linking fatty acid that is monounsaturated so that when the fatty acids link together, all of the sites of unsaturation are eliminated. The linking residue(s) may also be referred to as secondary or beta (β) chains.

In certain embodiments, the linking residues present in an estolide differ from one another. In certain embodiments, one or more of the linking residues differs from the base chain residue.

As noted above, in certain embodiments, suitable unsaturated fatty acids for preparing the estolides may include any mono- or polyunsaturated fatty acid. For example, monounsaturated fatty acids, along with a suitable catalyst, will form a single carbocation that allows for the addition of a second fatty acid, whereby a single link between two fatty acids is formed. Suitable monounsaturated fatty acids may include, but are not limited to, palmitoleic acid (16:1), vaccenic acid (18:1), oleic acid (18:1), eicosenoic acid (20:1), erucic acid (22:1), and nervonic acid (24:1). In addition, in certain embodiments, polyunsaturated fatty acids may be used to create estolides. Suitable polyunsaturated fatty acids may include, but are not limited to, hexadecatrienoic acid (16:3), alpha-linolenic acid (18:3), stearidonic acid (18:4), eicosatrienoic acid (20:3), eicosatetraenoic acid (20:4), eicosapentaenoic acid (20:5), heneicosapentaenoic acid (21:5), docosapentaenoic acid (22:5), docosahexaenoic acid (22:6), tetracosapentaenoic acid (24:5), tetracosahexaenoic acid (24:6), linoleic acid (18:2), gamma-linoleic acid (18:3), eicosadienoic acid (20:2), dihomo-gamma-linolenic acid (20:3), arachidonic acid (20:4), docosadienoic acid (20:2), adrenic acid (22:4), docosapentaenoic acid (22:5), tetracosatetraenoic acid (22:4), tetracosapentaenoic acid (24:5), pinolenic acid (18:2), podocarpic acid (20:3), rumenic acid (18:2), alpha-calendic acid (18:3), beta-calendic acid (18:3), jacaric acid (18:3), alpha-eleostearic acid (18:3), beta-eleostearic (18:3), catalpic acid (18:3), punicic acid (18:3), rumelenic acid (18:3), alpha-parinaric acid (18:4), beta-parinaric acid (18:4), and bosseopentaenoic acid (20:5). In certain embodiments, hydroxy fatty acids may be polymerized or homopolymerized by reacting the carboxylic acid functionality of one fatty acid with the hydroxy functionality of a second fatty acid. Exemplary hydroxyl fatty acids include, but are not limited to, ricinoleic acid, 6-hydroxystearic acid, 9,10-dihydroxystearic acid, 12-hydroxystearic acid, and 14-hydroxystearic acid.

The process for preparing the estolide compounds described herein may include the use of any natural or synthetic fatty acid source. However, it may be desirable to source the fatty acids from a renewable biological feedstock. Suitable starting materials of biological origin may include plant fats, plant oils, plant waxes, animal fats, animal oils, animal waxes, fish fats, fish oils, fish waxes, algal oils and mixtures thereof. Other potential fatty acid sources may include waste and recycled food-grade fats and oils, fats, oils, and waxes obtained by genetic engineering, fossil fuel-based materials and other sources of the materials desired.

In certain embodiments, the estolide compounds described herein may be prepared from non-naturally occurring fatty acids derived from naturally occurring feedstocks. In certain embodiments, the estolides are prepared from synthetic fatty acid reactants derived from naturally occurring feedstocks such as vegetable oils. For example, the synthetic fatty acid reactants may be prepared by cleaving fragments from larger fatty acid residues occurring in natural oils such as triglycerides using, for example, a cross-metathesis catalyst and alpha-olefin(s). The resulting truncated fatty acid residue(s) may be liberated from the glycerine backbone using any suitable hydrolytic and/or transesterification processes known to those of skill in the art. An exemplary fatty acid reactant includes 9-dodecenoic acid, which may be prepared via the cross metathesis of an oleic acid residue with 1-butene.

In certain embodiments, the estolide comprises fatty-acid chains of varying lengths. In some embodiments, z, p, and q are integers independently selected from 0 to 15, 0 to 12, 0 to 8, 0 to 6, 0 to 4, and 0 to 2. For example, in some embodiments, z is an integer selected from 0 to 15, 0 to 12, and 0 to 8. In some embodiments, z is an integer selected from 2 to 8. In some embodiments, z is 6. In some embodiments, z is 7. In some embodiments, z is an integer selected from 7 and 8. In some embodiments, p is an integer selected from 0 to 15, 0 to 6, and 0 to 3. In some embodiments, p is an integer selected from 1 to 5. In some embodiments, p is an integer selected from 1, 2, and 3, or 4, 5, and 6. In some embodiments, p is 1. In some embodiments, q is an integer selected from 0 to 15, 0 to 10, 0 to 6, and 0 to 3. In some embodiments, q is an integer selected from 1 to 8. In some embodiments, q is an integer selected from 0 and 1, 2 and 3, or 5, 6, and 7. In some embodiments, q is 6. In some embodiments, q is 7. In some embodiments, q is an integer selected from 7 and 8. In some embodiments, z, p and q, independently for each occurrence, are selected from 0, 1, 2, 3, 4, 5, 6, 7, 8, 9, 10, 11, 12, 13, 14 and 15. In some embodiments, z+p+q is an integer selected from 12 to 20. In some embodiments, z+p+q is 14. In some embodiments, z+p+q is 13.

In some embodiments, the estolide comprises fatty-acid chains of varying lengths. In some embodiments, x is, independently for each occurrence, an integer selected from 0 to 20, 0 to 18, 0 to 16, 0 to 14, 0 to 10, 1 to 12, 1 to 10, 2 to 8, 6 to 8, or 4 to 6. In some embodiments, x is, independently for each occurrence, an integer selected from 7 and 8. In some embodiments, x is, independently for each occurrence, an integer selected from 0, 1, 2, 3, 4, 5, 6, 7, 8, 9, 10, 11, 12, 13, 14, 15, 16, 17, 18, 19, and 20. In certain embodiments, for at least one fatty acid chain residue, x is an integer selected from 7 and 8.

In some embodiments, y is, independently for each occurrence, an integer selected from 0 to 20, 0 to 18, 0 to 16, 0 to 14, 0 to 10, 1 to 12, 1 to 10, 2 to 8, 6 to 8, or 4 to 6. In some embodiments, y is, independently for each occurrence, an integer selected from 7 and 8. In some embodiments, y is, independently for each occurrence, an integer selected from 0, 1, 2, 3, 4, 5, 6, 7, 8, 9, 10, 11, 12, 13, 14, 15, 16, 17, 18, 19, and 20. In some embodiments, for at least one fatty acid chain residue, y is an integer selected from 0 to 6, or 1 and 2. In certain embodiments, y is, independently for each occurrence, an integer selected from 1 to 6, or 1 and 2.

In some embodiments, x+y is, independently for each chain, an integer selected from 0 to 40, 0 to 20, 10 to 20, or 12 to 18. In some embodiments, x+y is, independently for each chain, an integer selected from 13 to 15. In some embodiments, x+y is 15 for each chain. In some embodiments, x+y is, independently for each chain, an integer selected from 6, 7, 8, 9, 10, 11, 12, 13, 14, 15, 16, 17, 18, 19, 20, 21, 22, 23, and 24. In certain embodiments, for at least one fatty acid chain residue, x+y is an integer selected from 9 to 13. In certain embodiments, for at least one fatty acid chain residue, x+y is 9. In certain embodiments, x+y is, independently for each chain, an integer selected from 9 to 13. In certain embodiments, x+y is 9 for each fatty acid chain residue.

In some embodiments, $W^1$, $W^2$, $W^3$, $W^4$, $W^5$, $W^6$, and $W^7$, independently for each occurrence, are selected from —$CH_2$—, —CH=CH—, and —$CHR_5$—, wherein $R_5$ is selected from —$OS(O)_2R_6$, and $R_6$ is selected from —OH, optionally substituted aryl, and optionally substituted alkyl.

In certain embodiments, $W^3$ is —$CH_2$—. In certain embodiments, $W^1$ is —$CH_2$—. In certain embodiments, $W^3$, $W^5$, and $W^7$ for each occurrence are —$CH_2$—. In some embodiments, $W^4$ and $W^6$ for each occurrence are —$CH_2$—. In certain embodiments, at least one of $W^1$, $W^2$, $W^3$, $W^4$, $W^5$, $W^6$, or $W^7$ is selected from —$CHR_5$—. In certain embodiments, $W^2$ is selected from —$CHR_5$—. In certain embodiments, $W^2$ is selected from —$CHR_5$—, $W^1$, $W^3$, $W^4$, $W^5$, and $W^6$ are $CH_2$, x+y is 15 for each chain, z is 6, and q is 7. In certain embodiments, $W^2$ is selected from —$CHR_5$—, $W^1$, $W^3$, $W^4$, $W^5$, and $W^6$ are $CH_2$, x+y is 15 for each chain, z is 7, and q is 6.

In certain embodiments, $Q^1$, $Q^2$, and $Q^3$, independently for each occurrence, are selected from —$CH_3$, —$CH=CH_2$, —$CH(R_5)CH_3$, and —$CH_2R_5$, wherein $R_5$ is selected from —$OS(O)_2R_6$, and $R_6$ is selected from optionally substituted aryl and optionally substituted alkyl. In certain embodiments, at least one of $W^1$, $W^2$, $W^3$, $W^4$, $W^5$, $W^6$, or $W^7$ is selected from —$CHR_5$—, or at least one of $Q^1$, $Q^2$, or $Q^3$ is selected from —$CH_2R_5$. In certain embodiments, $Q^1$, $Q^2$, and $Q^3$ are —$CH_3$.

In certain embodiments, the estolide compound of Formula I, II, or III may comprise any number of fatty acid residues to form an "n-mer" estolide. For example, the estolide may be in its dimer (n=0), trimer (n=1), tetramer (n=2), pentamer (n=3), hexamer (n=4), heptamer (n=5), octamer (n=6), nonamer (n=7), or decamer (n=8) form. In some embodiments, n is an integer selected from 0 to 20, 0 to 18, 0 to 16, 0 to 14, 0 to 12, 0 to 10, 0 to 8, or 0 to 6. In some embodiments, n is an integer selected from 0 to 4. In some embodiments, n is 1, wherein said at least one compound of Formula I, II, or III comprises the trimer. In some embodiments, n is equal to or greater than 1. In some embodiments, n is an integer selected from 0, 1, 2, 3, 4, 5, 6, 7, 8, 9, 10, 11, 12, 13, 14, 15, 16, 17, 18, 19, and 20.

In certain embodiments, the compounds of Formulas I and III represent subgenera of Formula II. Thus, in some embodiments, reference to a compound of Formulas I or III may also be described in reference to Formula II. By way of example, a compound of Formula I can be described with reference to Formula II, wherein m=1 and $R_4$ represents the group $Q^1(W^1)_q CH_2(W^2)_p CH_2(W^3)_z$—.

In addition or in the alternative to being sulfonated, in certain embodiments, the capping group is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. For example, with reference to Formula II, in certain embodiments $R_1$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_1$ is selected from $C_{13}$ to $C_{17}$ alkyl, such as from $C_{13}$ alkyl, $C_{15}$ alkyl, and $C_{17}$ alkyl. In some embodiments, $R_1$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_2$ of Formula I, II, or III is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_2$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_2$ is selected from $C_{13}$ to $C_{17}$ alkyl, such as from $C_{13}$ alkyl, $C_{15}$ alkyl, and $C_{17}$ alkyl. In some embodiments, $R_2$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_3$ is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_3$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_3$ is selected from $C_{13}$ to $C_{17}$ alkyl, such as from $C_{13}$ alkyl, $C_{15}$ alkyl, and $C_{17}$ alkyl. In some embodiments, $R_3$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_4$ is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_4$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_4$ is selected from $C_{13}$ to $C_{17}$ alkyl, such as from $C_{13}$ alkyl, $C_{15}$ alkyl, and $C_{17}$ alkyl. In some embodiments, $R_4$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

As noted above, in certain embodiments, it may be possible to manipulate one or more of the estolides' properties by altering the length of $R_1$ and/or its degree of saturation. However, in certain embodiments, the level of substitution on $R_1$ may also be altered to change or even improve the estolides' properties. Without being bound to any particular theory, in certain embodiments, it is believed that the presence of polar substituents on $R_1$, such as one or more hydroxy and/or sulfonate groups, may increase the viscosity of the estolide, while increasing pour point. Accordingly, in some embodiments, $R_1$ will be unsubstituted or optionally substituted with a group that is not hydroxyl or a sulfonate. Alternatively, in some embodiments, it may be desirable to increase the overall polarity of the molecule by providing one or more polar substituents on $R_1$, such as one or more epoxy groups, sulfur groups, and/or hydroxyl groups.

In some embodiments, the estolide is in its free-acid form, wherein $R_2$ of Formula I, II, or III is hydrogen. In some embodiments, $R_2$ is selected from optionally substituted alkyl that is saturated or unsaturated, and branched or unbranched. In certain embodiments, the $R_2$ residue may comprise any desired alkyl group, such as those derived from esterification of the estolide with the alcohols identified in the examples herein. In some embodiments, the alkyl group is selected from $C_1$ to $C_{40}$, $C_1$ to $C_{22}$, $C_3$ to $C_{20}$, $C_1$ to $C_{18}$, or $C_6$ to $C_{12}$ alkyl. In some embodiments, $R_2$ may be selected from $C_3$ alkyl, $C_4$ alkyl, $C_8$ alkyl, $C_{12}$ alkyl, $C_{16}$ alkyl, $C_{18}$ alkyl, and $C_{20}$ alkyl. For example, in certain embodiments, $R_2$ may be branched, such as isopropyl, isobutyl, or 2-ethylhexyl. In some embodiments, $R_2$ may be a larger alkyl group, branched or unbranched, comprising $C_{12}$ alkyl, $C_{16}$ alkyl, $C_{18}$ alkyl, or $C_{20}$ alkyl. Such groups at the $R_2$ position may be derived from esterification of the free-acid estolide using the Jarcol™ line of alcohols marketed by Jarchem Industries, Inc. of Newark, N.J., including Jarcol™ I-18CG, I-20, I-12, I-16, I-18T, and 85BJ. In some cases, $R_2$ may be sourced from certain alcohols to provide branched alkyls such as isostearyl and isopalmityl. It should be understood that such isopalmityl and isostearyl alkyl groups may cover any branched variation of $C_{16}$ and $C_{18}$, respectively. For example, the estolides described herein may comprise highly-branched isopalmityl or isostearyl groups at the $R_2$ position, derived from the Fineoxocol® line of isopalmityl and isostearyl alcohols marketed by Nissan Chemical America Corporation of Houston, Tex., including Fineoxocol® 180, 180N, and 1600. Without being bound to any particular theory, in embodiments, large, highly-branched alkyl groups (e.g., isopalmityl and isostearyl) at the $R_2$ position of the estolides can provide at least one way to increase the lubricant's viscosity, while substantially retaining or even reducing its pour point.

In some embodiments, the compounds described herein may comprise a mixture of two or more estolide compounds of Formula I, II, and III. It is possible to characterize the chemical makeup of an estolide, a mixture of estolides, or a composition comprising estolides, by using the compound's, mixture's, or composition's measured estolide number (EN)

of compound or composition. The EN represents the average number of fatty acids added to the base fatty acid. The EN also represents the average number of estolide linkages per molecule:

EN=$n$+1 wherein n is the number of secondary (β) fatty acids. Accordingly, a single estolide compound will have an EN that is a whole number, for example for dimers, trimers, and tetramers:

dimer EN=1 trimer EN=2 tetramer EN=3

However, a composition comprising two or more estolide compounds may have an EN that is a whole number or a fraction of a whole number. For example, a composition having a 1:1 molar ratio of dimer and trimer would have an EN of 1.5, while a composition having a 1:1 molar ratio of tetramer and trimer would have an EN of 2.5.

In some embodiments, the compositions may comprise a mixture of two or more estolides having an EN that is an integer or fraction of an integer that is greater than 4.5, or even 5.0. In some embodiments, the EN may be an integer or fraction of an integer selected from about 1.0 to about 5.0. In some embodiments, the EN is an integer or fraction of an integer selected from 1.2 to about 4.5. In some embodiments, the EN is selected from a value greater than 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6 and 5.8. In some embodiments, the EN is selected from a value less than 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, and 5.0, 5.2, 5.4, 5.6, 5.8, and 6.0. In some embodiments, the EN is selected from 1, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, and 6.0.

As noted above, it should be understood that the chains of the estolide compounds may be independently optionally substituted, wherein one or more hydrogens are removed and replaced with one or more of the substituents identified herein. Similarly, two or more of the hydrogen residues may be removed to provide one or more sites of unsaturation, such as a cis or trans double bond. Further, the chains may optionally comprise branched hydrocarbon residues. For example, in some embodiments the estolides described herein may comprise at least one compound of Formula II:

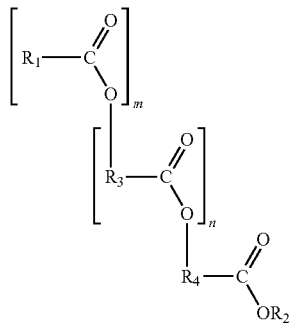

Formula II wherein
m is an integer equal to or greater than 1;
n is an integer equal to or greater than 0;

$R_1$, independently for each occurrence, is an optionally substituted alkyl that is saturated or unsaturated, and branched or unbranched $R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched, wherein at least one of $R_1$, $R_3$, or $R_4$ is substituted with one or more of a sulfate residue, an alkyl sulfonate residue, or an aryl sulfonate residue.

In certain embodiments, m is 1. In some embodiments, m is an integer selected from 2, 3, 4, and 5. In some embodiments, n is an integer selected from 1, 2, 3, 4, 5, 6, 7, 8, 9, 10, 11, and 12. In some embodiments, one or more $R_3$ differs from one or more other $R_3$ in a compound of Formula II. In some embodiments, one or more $R_3$ differs from $R_4$ in a compound of Formula II. In some embodiments, if the compounds of Formula II are prepared from one or more polyunsaturated fatty acids, it is possible that one or more of $R_3$ and $R_4$ will have one or more sites of unsaturation. Depending on the manner in which the estolide is synthesized, in certain embodiments, estolides prepared with polyunsaturates and a sulfonic acid will provide estolides wherein one or more of $R_1$, $R_3$, and $R_4$ will comprise one or more sulfonate residues. In some embodiments, if the compounds of Formula II are prepared from one or more branched fatty acids, it is possible that one or more of $R_3$ and $R_4$ will be branched.

In some embodiments, $R_3$ and $R_4$ can be $CH_3(CH_2)_y CH(CH_2)_x$—, where x is, independently for each occurrence, an integer selected from 0, 1, 2, 3, 4, 5, 6, 7, 8, 9, 10, 11, 12, 13, 14, 15, 16, 17, 18, 19, and 20, and y is, independently for each occurrence, an integer selected from 0, 1, 2, 3, 4, 5, 6, 7, 8, 9, 10, 11, 12, 13, 14, 15, 16, 17, 18, 19, and 20. Where both $R_3$ and $R_4$ are $CH_3(CH_2)_y CH(CH_2)_x$—, the compounds may be compounds according to Formula III.

Without being bound to any particular theory, in certain embodiments, altering the EN produces estolides having desired viscometric properties while substantially retaining or even reducing pour point. For example, in some embodiments the estolides exhibit a decreased pour point upon increasing the EN value. Accordingly, in certain embodiments, a method is provided for retaining or decreasing the pour point of an estolide base oil by increasing the EN of the base oil, or a method is provided for retaining or decreasing the pour point of a composition comprising an estolide base oil by increasing the EN of the base oil. In some embodiments, the method comprises: selecting an estolide base oil having an initial EN and an initial pour point; and removing at least a portion of the base oil, said portion exhibiting an EN that is less than the initial EN of the base oil, wherein the resulting estolide base oil exhibits an EN that is greater than the initial EN of the base oil, and a pour point that is equal to or lower than the initial pour point of the base oil. In some embodiments, the selected estolide base oil is prepared by oligomerizing at least one first unsaturated fatty acid with at least one second unsaturated fatty acid and/or saturated fatty acid. In some embodiments, the removing at least a portion of the base oil is accomplished by distillation, chromatography, membrane separation, phase separation, affinity separation, solvent extraction, or combinations thereof. In some embodiments, the distillation takes place at a temperature and/or pressure that is suitable to separate the estolide base oil into different "cuts" that individually exhibit different EN values. In some embodiments, this may be accomplished by subjecting the base oil temperature of at least about 250° C. and an absolute pressure of no greater than about 25 microns. In some embodiments, the distillation takes place at a temperature range of about 250° C. to about 310° C. and an absolute pressure range of about 10 microns to about 25 microns.

In some embodiments, estolide compounds and compositions exhibit an EN that is greater than or equal to 1, such as an integer or fraction of an integer selected from about 1.0 to about 2.0. In some embodiments, the EN is an integer or fraction of an integer selected from about 1.0 to about 1.6. In some embodiments, the EN is a fraction of an integer selected from about 1.1 to about 1.5. In some embodiments, the EN is selected from a value greater than 1.0, 1.1, 1.2, 1.3, 1.4, 1.5, 1.6, 1.7, 1.8, and 1.9. In some embodiments, the EN is selected from a value less than 1.1, 1.2, 1.3, 1.4, 1.5, 1.6, 1.7, 1.8, 1.9, and 2.0.

In some embodiments, the EN is greater than or equal to 1.5, such as an integer or fraction of an integer selected from about 1.8 to about 2.8. In some embodiments, the EN is an integer or fraction of an integer selected from about 2.0 to about 2.6. In some embodiments, the EN is a fraction of an integer selected from about 2.1 to about 2.5. In some embodiments, the EN is selected from a value greater than 1.8, 1.9, 2.0, 2.1, 2.2, 2.3, 2.4, 2.5, 2.6, and 2.7. In some embodiments, the EN is selected from a value less than 1.9, 2.0, 2.1, 2.2, 2.3, 2.4, 2.5, 2.6, 2.7, and 2.8. In some embodiments, the EN is about 1.8, 2.0, 2.2, 2.4, 2.6, or 2.8.

In some embodiments, the EN is greater than or equal to about 4, such as an integer or fraction of an integer selected from about 4.0 to about 5.0. In some embodiments, the EN is a fraction of an integer selected from about 4.2 to about 4.8. In some embodiments, the EN is a fraction of an integer selected from about 4.3 to about 4.7. In some embodiments, the EN is selected from a value greater than 4.0, 4.1, 4.2, 4.3, 4.4, 4.5, 4.6, 4.7, 4.8, and 4.9. In some embodiments, the EN is selected from a value less than 4.1, 4.2, 4.3, 4.4, 4.5, 4.6, 4.7, 4.8, 4.9, and 5.0. In some embodiments, the EN is about 4.0, 4.2, 4.4, 4.6, 4.8, or 5.0.

In some embodiments, the EN is greater than or equal to about 5, such as an integer or fraction of an integer selected from about 5.0 to about 6.0. In some embodiments, the EN is a fraction of an integer selected from about 5.2 to about 5.8. In some embodiments, the EN is a fraction of an integer selected from about 5.3 to about 5.7. In some embodiments, the EN is selected from a value greater than 5.0, 5.1, 5.2, 5.3, 5.4, 5.5, 5.6, 5.7, 5.8, and 5.9. In some embodiments, the EN is selected from a value less than 5.1, 5.2, 5.3, 5.4, 5.5, 5.6, 5.7, 5.8, 5.9, and 6.0. In some embodiments, the EN is about 5.0, 5.2, 5.4, 5.4, 5.6, 5.8, or 6.0.

In some embodiments, the EN is greater than or equal to 1, such as an integer or fraction of an integer selected from about 1.0 to about 2.0. In some embodiments, the EN is a fraction of an integer selected from about 1.1 to about 1.7. In some embodiments, the EN is a fraction of an integer selected from about 1.1 to about 1.5. In some embodiments, the EN is selected from a value greater than 1.0, 1.1, 1.2, 1.3, 1.4, 1.5, 1.6, 1.7, 1.8, or 1.9. In some embodiments, the EN is selected from a value less than 1.2, 1.3, 1.4, 1.5, 1.6, 1.7, 1.8, 1.9, or 2.0. In some embodiments, the EN is about 1.0, 1.2, 1.4, 1.6, 1.8, or 2.0. In some embodiments, the EN is greater than or equal to 1, such as an integer or fraction of an integer selected from about 1.2 to about 2.2. In some embodiments, the EN is an integer or fraction of an integer selected from about 1.4 to about 2.0. In some embodiments, the EN is a fraction of an integer selected from about 1.5 to about 1.9. In some embodiments, the EN is selected from a value greater than 1.0, 1.1, 1.2, 1.3, 1.4, 1.5, 1.6, 1.7, 1.8, 1.9, 2.0, and 2.1. In some embodiments, the EN is selected from a value less than 1.2, 1.3, 1.4, 1.5, 1.6, 1.7, 1.8, 1.9, 2.0, 2.1, and 2.2. In some embodiments, the EN is about 1.0, 1.2, 1.4, 1.6, 1.8, 2.0, or 2.2.

In some embodiments, the EN is greater than or equal to 2, such as an integer or fraction of an integer selected from about 2.8 to about 3.8. In some embodiments, the EN is an integer or fraction of an integer selected from about 2.9 to about 3.5. In some embodiments, the EN is an integer or fraction of an integer selected from about 3.0 to about 3.4. In some embodiments, the EN is selected from a value greater than 2.0, 2.1, 2.2, 2.4, 2.5, 2.6, 2.7, 2.8, 2.9, 3.0, 3.1, 3.4, 3.5, 3.6, and 3.7. In some embodiments, the EN is selected from a value less than 2.2, 2.3, 2.4, 2.5, 2.6, 2.7, 2.8, 2.9, 3.0, 3.1, 3.2, 3.3, 3.4, 3.5, 3.6, 3.7, and 3.8. In some embodiments, the EN is about 2.0, 2.2, 2.4, 2.6, 2.8, 3.0, 3.2, 3.4, 3.6, or 3.8. Typically, base stocks and lubricant compositions exhibit certain lubricity, viscosity, and/or pour point characteristics. For example, in certain embodiments, suitable viscosity characteristics of the base oil may range from about 10 cSt to about 250 cSt at 40° C., and/or about 3 cSt to about 30 cSt at 100° C. In some embodiments, the compounds and compositions may exhibit viscosities within a range from about 50 cSt to about 150 cSt at 40° C., and/or about 10 cSt to about 20 cSt at 100° C.

In some embodiments, the estolide compounds and compositions may exhibit viscosities less than about 55 cSt at 40° C. or less than about 45 cSt at 40° C., and/or less than about 12 cSt at 100° C. or less than about 10 cSt at 100° C. In some embodiments, the estolide compounds and compositions may exhibit viscosities within a range from about 25 cSt to about 55 cSt at 40° C., and/or about 5 cSt to about 11 cSt at 100° C. In some embodiments, the estolide compounds and compositions may exhibit viscosities within a range from about 35 cSt to about 45 cSt at 40° C., and/or about 6 cSt to about 10 cSt at 100° C. In some embodiments, the estolide compounds and compositions may exhibit viscosities within a range from about 38 cSt to about 43 cSt at 40° C., and/or about 7 cSt to about 9 cSt at 100° C.

In some embodiments, the estolide compounds and compositions may exhibit viscosities less than about 120 cSt at 40° C. or less than about 100 cSt at 40° C., and/or less than about 18 cSt at 100° C. or less than about 17 cSt at 100° C. In some embodiments, the estolide compounds and compositions may exhibit a viscosity within a range from about 70 cSt to about 120 cSt at 40° C., and/or about 12 cSt to about 18 cSt at 100° C. In some embodiments, the estolide compounds and compositions may exhibit viscosities within a range from about 80 cSt to about 100 cSt at 40° C., and/or about 13 cSt to about 17 cSt at 100° C. In some embodiments, the estolide compounds and compositions may exhibit viscosities within a range from about 85 cSt to about 95 cSt at 40° C., and/or about 14 cSt to about 16 cSt at 100° C.

In some embodiments, the estolide compounds and compositions may exhibit viscosities greater than about 180 cSt at 40° C. or greater than about 200 cSt at 40° C., and/or greater than about 20 cSt at 100° C. or greater than about 25 cSt at 100° C. In some embodiments, the estolide compounds and compositions may exhibit a viscosity within a range from about 180 cSt to about 230 cSt at 40° C., and/or about 25 cSt to about 31 cSt at 100° C. In some embodiments, estolide compounds and compositions may exhibit viscosities within a range from about 200 cSt to about 250 cSt at 40° C., and/or about 25 cSt to about 35 cSt at 100° C. In some embodiments, estolide compounds and compositions may exhibit viscosities within a range from about 210 cSt to about 230 cSt at 40° C., and/or about 28 cSt to about 33 cSt at 100° C. In some embodiments, the estolide compounds and compositions may exhibit viscosities within a range from about 200 cSt to about 220 cSt at 40° C., and/or about 26 cSt to about 30 cSt at 100° C. In some embodiments, the estolide compounds and compositions may exhibit viscosities within a range from about 205 cSt to about 215 cSt at 40° C., and/or about 27 cSt to about 29 cSt at 100° C.

In some embodiments, the estolide compounds and compositions may exhibit viscosities less than about 45 cSt at 40° C. or less than about 38 cSt at 40° C., and/or less than about 10 cSt at 100° C. or less than about 9 cSt at 100° C. In some embodiments, the estolide compounds and compositions may exhibit a viscosity within a range from about 20 cSt to about 45 cSt at 40° C., and/or about 4 cSt to about 10 cSt at 100° C. In some embodiments, the estolide compounds and compositions may exhibit viscosities within a range from about 28 cSt to about 38 cSt at 40° C., and/or about 5 cSt to about 9 cSt at 100° C. In some embodiments, the estolide compounds and compositions may exhibit viscosities within a range from about 30 cSt to about 35 cSt at 40° C., and/or about 6 cSt to about 8 cSt at 100° C.

In some embodiments, the estolide compounds and compositions may exhibit viscosities less than about 80 cSt at 40° C. or less than about 70 cSt at 40° C., and/or less than about 14 cSt at 100° C. or less than about 13 cSt at 100° C. In some embodiments, the estolide compounds and compositions may exhibit a viscosity within a range from about 50 cSt to about 80 cSt at 40° C., and/or about 8 cSt to about 14 cSt at 100° C. In some embodiments, the estolide compounds and compositions may exhibit viscosities within a range from about 60 cSt to about 70 cSt at 40° C., and/or about 9 cSt to about 13 cSt at 100° C. In some embodiments, the estolide compounds and compositions may exhibit viscosities within a range from about 63 cSt to about 68 cSt at 40° C., and/or about 10 cSt to about 12 cSt at 100° C.

In some embodiments, the estolide compounds and compositions may exhibit viscosities greater than about 120 cSt at 40° C. or greater than about 130 cSt at 40° C., and/or greater than about 15 cSt at 100° C. or greater than about 18 cSt at 100° C. In some embodiments, the estolide compounds and compositions may exhibit a viscosity within a range from about 120 cSt to about 150 cSt at 40° C., and/or about 16 cSt to about 24 cSt at 100° C. In some embodiments, the estolide compounds and compositions may exhibit viscosities within a range from about 130 cSt to about 160 cSt at 40° C., and/or about 17 cSt to about 28 cSt at 100° C. In some embodiments, the estolide compounds and compositions may exhibit viscosities within a range from about 130 cSt to about 145 cSt at 40° C., and/or about 17 cSt to about 23 cSt at 100° C. In some embodiments, the estolide compounds and compositions may exhibit viscosities within a range from about 135 cSt to about 140 cSt at 40° C., and/or about 19 cSt to about 21 cSt at 100° C. In some embodiments, the estolide compounds and compositions may exhibit viscosities of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 34, 36, 38, 40, 42, 44, 46, 48, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, or 400 cSt. at 40° C. In some embodiments, the estolide compounds and compositions may exhibit viscosities of about 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30 cSt at 100° C. In certain embodiments, estolides may exhibit desirable low-temperature pour point properties. In some embodiments, the estolide compounds and compositions may exhibit a pour point lower than about −25° C., about −35° C., −40° C., or even about −50° C. In some embodiments, the estolide compounds and compositions have a pour point of about −25° C. to about −45° C. In some embodiments, the pour point falls within a range of about −30° C. to about −40° C., about −34° C. to about −38° C., about −30° C. to about −45° C., −35° C. to about −45° C., 34° C. to about −42° C., about −38° C. to about −42° C., or about 36° C. to about −40° C. In some embodiments, the pour point falls within the range of about —27° C. to about −37° C., or about −30° C. to about −34° C. In some embodiments, the pour point falls within the range of about −25° C. to about −35° C., or about −28° C. to about −32° C. In some embodiments, the pour point falls within the range of about −28° C. to about −38° C., or about −31° C. to about −35° C. In some embodiments, the pour point falls within the range of about −31° C. to about −41° C., or about −34° C. to about −38° C. In some embodiments, the pour point falls within the range of about −40° C. to about −50° C., or about −42° C. to about −48° C. In some embodiments, the pour point falls within the range of about −50° C. to about −60° C., or about −52° C. to about −58° C. In some embodiments, the upper bound of the pour point is less than about −35° C., about −36° C., about −37° C., about −38° C., about −39° C., about −40° C., about −41° C., about −42° C., about −43° C., about −44° C., or about −45° C. In some embodiments, the lower bound of the pour point is greater than about −70° C., about −69° C., about −68° C., about −67° C., about −66° C., about −65° C., about −64° C., about −63° C., about −62° C., about −61° C., about −60° C., about −59° C., about −58° C., about −57° C., about −56° C., —55° C., about −54° C., about −53° C., about −52° C., —51, about −50° C., about −49° C., about −48° C., about −47° C., about −46° C., or about −45° C.

In addition, in certain embodiments, the estolides may exhibit decreased Iodine Values (IV) when compared to estolides prepared by other methods. IV is a measure of the degree of total unsaturation of an oil, and is determined by measuring the amount of iodine per gram of estolide (cg/g). In certain instances, oils having a higher degree of unsaturation may be more susceptible to creating corrosiveness and deposits, and may exhibit lower levels of oxidative stability. Compounds having a higher degree of unsaturation will have more points of unsaturation for iodine to react with, resulting in a higher IV. Thus, in certain embodiments, it may be desirable to reduce the IV of estolides in an effort to increase the oil's oxidative stability, while also decreasing harmful deposits and the corrosiveness of the oil.

In some embodiments, estolide compounds and compositions described herein have an IV of less than about 40 cg/g or less than about 35 cg/g. In some embodiments, estolides have an IV of less than about 30 cg/g, less than about 25 cg/g, less than about 20 cg/g, less than about 15 cg/g, less than about 10 cg/g, or less than about 5 cg/g. The IV of a composition may be reduced by decreasing the estolide's degree of unsaturation. This may be accomplished by, for example, by increasing the amount of saturated capping materials relative to unsaturated capping materials when synthesizing the estolides. Alternatively, in certain embodiments, IV may be reduced by hydrogenating estolides having unsaturated caps.

Also described herein are certain processes for preparing estolide base oils. In certain embodiments, the method comprises providing at least one first estolide compound having at least one sulfonate residue, and removing the at least one sulfonate residue to provide an estolide base oil. In certain embodiments, the at least one first estolide compound is prepared by a process comprising oligomerizing at least one first fatty acid reactant with at least one second fatty acid reactant in the presence of a sulfonic acid catalyst. In certain embodiments, the at least one first fatty acid reactant has at least one site of unsaturation. In certain embodiments, the at least one first fatty acid reactant is selected from one or more of an unsaturated fatty acid, an unsaturated fatty acid ester, and an unsaturated fatty acid oligomer. In certain embodiments, the at least one second fatty acid reactant is selected from one or more of a saturated fatty acid and an unsaturated fatty acid. In certain embodiments, the first and second fatty acid reactants do not comprise free hydroxy groups bound to their hydrocarbon backbones. Thus, in certain embodiments, the first and second fatty acid reactants do not comprise hydroxy fatty acids (e.g., ricinoleic acid). In certain embodiment, the oligomerizing comprises the covalent linking of the carboxylate residue of the second fatty acid reactant to a site of unsaturation of the first fatty acid reactant.

In certain embodiments, at least one first estolide compound is prepared by a process that includes oligomerizing at least one first fatty acid reactant with at least one second fatty acid reactant in the presence of a sulfonic acid catalyst, wherein the oligomerizing occurs at a temperature of about 100° C. or less. In certain embodiments, the oligomerizing occurs at a temperature of about 85° C. or less, about 70° C. or less, about 60° C. or less, or about 50° C. or less. In certain embodiments, the oligomerizing occurs at a temperature of about 25° C. to about 75° C., about 15° C. to about 60° C., or about 25° C. to about 45° C. In certain embodiments, the oligomerizing occurs at a pressure of about 1 atm. In certain embodiments, the oligomerizing occurs at a pressure of about 1 atm or less. In certain embodiments, the oligomerizing occurs at a pressure of about 1 atm or more.

In certain embodiments, the sulfonic acid catalyst is sulfuric acid. In certain embodiments, the sulfonic acid catalyst is selected from one or more of an optionally substituted alkyl sulfonic acid catalyst and an optionally substituted aryl sulfonic acid catalyst. In certain embodiments, the sulfonic acid catalyst is selected from one or more of an optionally substituted alkyl sulfonic acid. In certain embodiments, the sulfonic acid catalyst is selected from unsubstituted aryl sulfonic acid catalysts, optionally substituted alkyl aryl sulfonic acid catalysts, unsubstituted alkyl sulfonic acid catalysts, and substituted alkyl sulfonic acid catalysts. In certain embodiments, the sulfonic acid catalyst is homogenous or heterogeneous. In certain embodiments, the sulfonic acid catalyst is a solid-supported catalyst. In certain embodiments, the sulfonic acid catalyst is a polysulfonic acid, such as methane disulfonic acid or methane trisulfonic acid. In certain embodiments, the sulfonic acid is selected from triflic acid, p-toluenesulfonic acid, and methanesulfonic acid.

In certain embodiments, it has been surprisingly discovered that contacting one or more unsaturated fatty acids with a sulfonic acid catalyst (e.g., methanesulfonic acid) will result in the formation of estolide compounds having one or more sulfonate residues. Without being bound to any particular theory, in certain embodiments, it is believed that in addition to catalyzing the oligomerization of fatty acids to form estolides, at least a portion of the sulfonic acid catalyst used in the synthesis may add to one or more sites of unsaturation (e.g., an unsaturated capping residue) of the resulting estolide compounds, wherein an oxygen of the sulfonic acid catalyst forms a covalent bond with a carbon of a site of unsaturation. For example, methanesulfonic acid may be used to catalyze the formation of estolide compounds. However, under certain synthetic conditions, the methanesulfonic acid may also add to sites of unsaturation on the estolide intermediate to provide a sulfonated product, i.e., mesylated estolides. In certain embodiments, the sulfonation occurs in situ during estolide formation. In certain embodiments, catalytic conditions of the estolide synthesis may cause one or more sites of unsaturation to "migrate" along the respective hydrocarbon chains of the estolide compound. Thus, addition of the sulfonate residue to the estolide compound may result in the placement of the sulfonate residue at one of multiple positions along the hydrocarbon chain of the capping fatty acid residue.

In certain embodiments, the strength of the sulfonic acid and the overall reaction conditions will determine whether sulfonation of the resulting estolide compound occurs. Without being bound to any particular theory, in certain embodiments, because nucleophilicity decreases as the electronegativity of the sulfonic acid substituent increases, some sulfonic acid catalysts will not add to fatty acid residues having sites of unsaturation under certain reaction conditions (e.g., temperature, pressure, and/or solvent conditions). For example, in certain embodiments, more acidic sulfonic acid catalysts having higher electronegativities, e.g., substituted alkyl sulfonic acids (such as triflic acid) and arylsulfonic acids (such as toluenesulfonic acid) will not provide sulfonated products, while less acidic catalysts such as unsubstituted alkylsulfonic acids (e.g., methanesulfonic acid) will result in sulfonated products. Accordingly, in certain embodiments, the sulfonic acid catalyst is an unsubstituted alkylsulfonic acid catalyst. In certain embodiments, the unsubstituted alkylsulfonic acid is methanesulfonic acid.

In certain embodiments, it may be desirable to remove the at least one sulfonate residue from sulfonated estolides. For example, in certain embodiments, high-stress conditions may cause sulfonated estolide products to degrade and liberate sulfonic acid, which may, in turn, result in further compound degradation and corrosion to the system in which the estolide is being used (e.g., motors and engines). Accordingly, in certain embodiments, the synthetic process comprises removing the at least one sulfonate residue (e.g., mesylate residue) from the at least one estolide compound to provide a desulfonated estolide base oil. In certain embodiments, removing the at least one sulfonate residue includes eliminating said at least one sulfonate residue to provide a site of unsaturation. In certain embodiments, eliminating said at least one sulfonate residue includes contacting the at least one first estolide compound with a base. In certain embodiments, the base is selected from one or more of a metal hydroxide, a carboxylate salt, or a nitrogenous compound. Exemplary metal hydroxides include sodium hydroxide and potassium hydroxide. Exemplary carboxylate salts include short and long chain fatty acid salts, such as acetate salts (e.g., $Na^+$, $Li^+$ or $K^+$ acetate) and branched fatty acid salts (e.g., $Na^+$, $Li^+$ or $K^+$ 2-ethylhexanoate). In certain embodiments, the nitrogenous compound is an amine such as a tertiary amine or an aromatic amine. Tertiary amines include, but are not limited to, trimethylamine, triethylamine, tripropylamine, 1-methylpiperidine, 1,4-dimethylpiperazine, and N,N-diisopropylethylamine (Hunig's Base). Aromatic amines include, but are not limited to, pyridine, 2-picoline, 2,6-lutidine, quinoline, and 5,6,7,8-tetrahydroquinoline.

In certain embodiments, elimination of the sulfonate residue (e.g., mesylate) will result in the regeneration of the original oligomerization catalyst (e.g., methanesulfonic acid), which may be recycled for reuse. The term "demesylation" may be used to describe the elimination of the mesylate residue.

As noted above, in certain embodiments, the methods described will generate unsaturated estolides, which may undergo a further reaction with the sulfonic acid catalyst itself to provide sulfonated estolides. However, in certain embodiments, the reaction kinetics of the methods described herein may result in the addition of the sulfonic acid catalyst to the site of unsaturation of the fatty acid reactant, thus competing with the formation of the estolide. That is, in certain embodiments, the covalent bonding of a sulfonic acid molecule to the double bond of a first fatty acid will inhibit the ability of a second fatty acid to bond to the first fatty acid. Accordingly, in certain embodiments, the synthetic methods described herein include the formation of a sulfonated fatty acid, e.g., mesylated stearic acid (derived from addition of methanesulfonic acid to oleic acid). In certain embodiments, the sulfonate residue is removed to provide the original fatty acid reactant or isomer thereof and the sulfonic acid catalyst. In certain embodiments, the fatty acid reactant and sulfonic acid catalyst are recycled and reused.

In certain embodiments, eliminating the at least one sulfonate residue includes heating the at least one estolide compound, such as exposing the at least one estolide compound to distillation conditions. In certain embodiments, at least one estolide compound is heated to a temperature that is greater than about 20° C. In certain embodiments, at least one estolide compound is heated to a temperature of at least about 50° C. In certain embodiments, at least one estolide compound is heated to a temperature of at least about 60° C., at least about 70° C., at least about 80° C., at least about 90° C., at least about 100° C., at least about 110° C., at least about 120° C., at least about 130° C., at least about 140° C., at least about 150° C., at least about 160° C., at least about 170° C., at least about 180° C., at least about 190° C., or at least about 200° C. In certain embodiments, the at least one estolide compound is heated in temperature range of about 50° C. to about 250° C., about 65° C. to about 225° C., about 75° C. to about 200° C., or about 100° C. to about 175° C.

In certain embodiments, eliminating the at least one sulfonate residue includes heating the at least one estolide compound under reduced pressure. In certain embodiments the elimination occurs, for at least a period of time, at a pressure of less than 1 atm abs (absolute), such at less than about 250 torr abs, less than about 100 torr abs, less than about 50 torr abs, or less than about 25 torr abs. In certain embodiments, elimination is carried out at a pressure of about 1 torr abs to about 20 torr abs, or about 5 torr abs to about 15 torr abs. In certain embodiments the elimination, for at least a period of time, is carried out at a pressure of greater than about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, and about 250 torrs abs. In some embodiments, the elimination, for at least a period of time, is carried out at a pressure of less than about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, or about 250 torrs abs.

In certain embodiments, removing the at least one sulfonate residue includes substituting said at least one sulfonate with a non-sulfonate residue. In certain embodiments, substituting said at least one sulfonate includes contacting the at least one first estolide compound with a nucleophile. In certain embodiments, the nucleophile is selected from one or more of an optionally substituted alkoxide, an optionally substituted amine, a halide, a sulfide, a cyanide, and an azide.

The present disclosure further relates to methods of making estolides according to Formula I, II, and III using a sulfonic acid catalyst, wherein said estolides may subsequently be treated to remove any sulfonate residues bound thereto to provide estolides according to Formula IV. By way of example, the reaction of an unsaturated fatty acid with sulfonic acid to provide a sulfonated estolide, and the removal of the sulfonate residues from the resulting sulfonated estolide, are illustrated and discussed in the following Schemes 1 and 2. The particular structural formulas used to illustrate the reactions correspond to those for synthesis of compounds to Formula I and III; however, the methods apply equally to the synthesis of compounds according to Formula II, with use of compounds having structure corresponding to $R_3$ and $R_4$ with a reactive site of unsaturation.

As illustrated below, compound 100 represents an unsaturated fatty acid that may serve as the basis for preparing the estolide compounds described herein.

Scheme 1

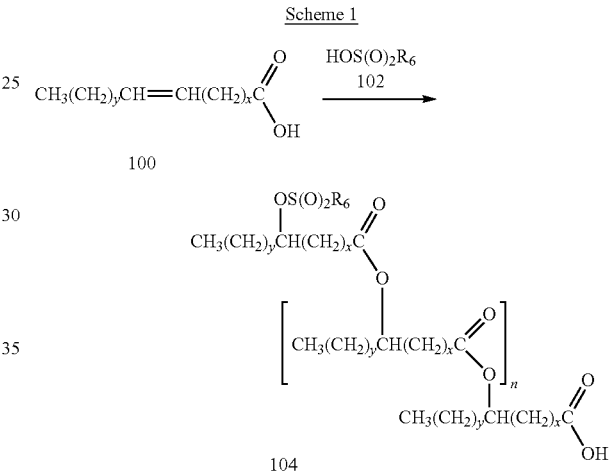

In Scheme 1, wherein x is, independently for each occurrence, an integer selected from 0 to 20, y is, independently for each occurrence, an integer selected from 0 to 20, n is an integer greater than or equal to 0, and $R_6$ is —OH, optionally substituted alkyl, or optionally substituted aryl, unsaturated fatty acid 100 may be contacted with sulfonic acid catalyst 102 to provide sulfonated estolide 104. Exemplary sulfonic acids include, but are not limited to, methanesulfonic acid, triflic acid, and p-toluenesulfonic (tosic) acid.

Scheme 2

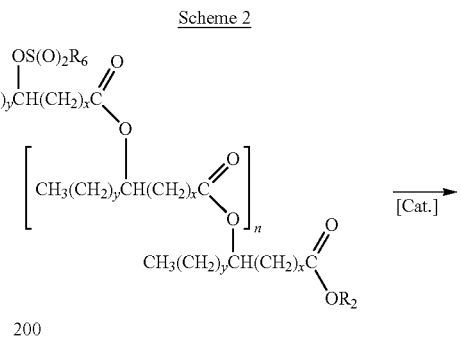

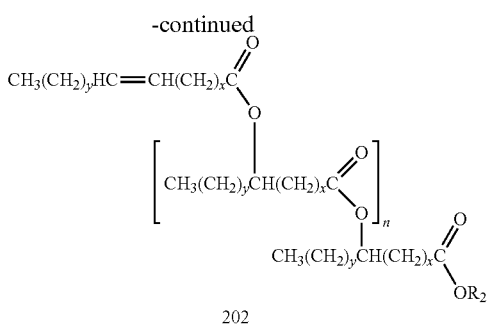

202

Similarly, in Scheme 2, wherein x is, independently for each occurrence, an integer selected from 0 to 20, y is, independently for each occurrence, an integer selected from 0 to 20, n is an integer greater than or equal to 0, $R_2$ is hydrogen or an optionally substituted alkyl that is saturated or unsaturated, and branched or unbranched, and $R_6$ is —OH, optionally substituted alkyl or optionally substituted aryl, sulfonated estolide 200 may be exposed to a catalysts such as base and/or heat, which eliminates the sulfonate residue to yield free-acid estolide 202. Exemplary bases include, but are not limited to, metal hydroxides, carboxylate salts, and nitrogenous compounds such as pyridine. Exemplary heating conditions include heating the sulfonated estolide to temperatures greater than about 100° C.

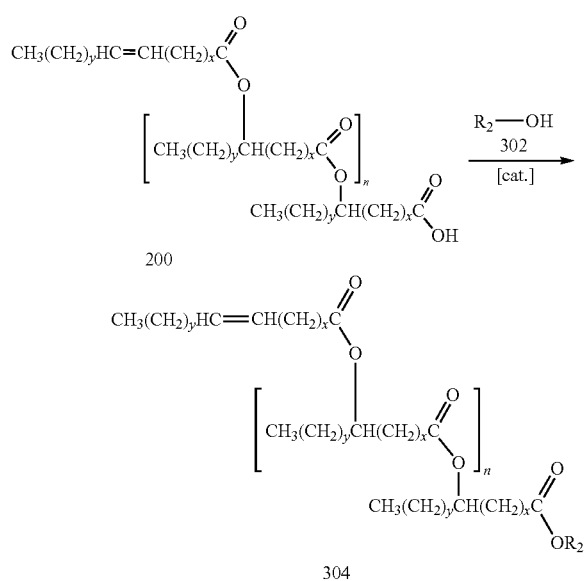

Similarly, in Scheme 3, wherein x is, independently for each occurrence, an integer selected from 0 to 20, y is, independently for each occurrence, an integer selected from 0 to 20, n is an integer greater than or equal to 1, and $R_2$ is an optionally substituted alkyl that is saturated or unsaturated, and branched or unbranched, free acid estolide 200 may be esterified by any suitable procedure known to those of skilled in the art, such as acid-catalyzed reduction with alcohol 302, to yield esterified estolide 304. Other exemplary methods may include other types of Fischer esterification, such as those using Lewis acid catalysts such as $BF_3$.

As discussed above, in certain embodiments, the estolides described herein may have improved properties which render them useful in lubricating compositions. Such applications may include, without limitation, crankcase oils, gearbox oils, hydraulic fluids, drilling fluids, two-cycle engine oils, greases, and the like. Other suitable uses may include marine applications, where biodegradability and toxicity are of concern. In certain embodiments, the nontoxic nature of certain estolides described herein may also make them suitable for use as lubricants in the cosmetic and food industries.

In some embodiments, it may be desirable to prepare lubricant compositions comprising one or more of the estolides described herein. For example, in certain embodiments, the estolides described herein may be blended with one or more additives selected from polyalphaolefins, synthetic esters, polyalkylene glycols, mineral oils (Groups I, II, and III), pour point depressants, viscosity modifiers, anti-corrosives, anti-wear agents, detergents, dispersants, colorants, antifoaming agents, and demulsifiers. In addition, or in the alternative, in certain embodiments, the estolides described herein may be co-blended with one or more synthetic or petroleum-based oils to achieve desired viscosity and/or pour point profiles. In certain embodiments, certain estolides described herein also mix well with gasoline, so that they may be useful as fuel components or additives.

In all of the foregoing examples, the compounds described may be useful alone, as mixtures, or in combination with other compounds, compositions, and/or materials.

Methods for obtaining the novel compounds described herein will be apparent to those of ordinary skill in the art, suitable procedures being described, for example, in the examples below, and in the references cited herein.

EXAMPLES

Analytics

Nuclear Magnetic Resonance:

NMR spectra were collected using a Bruker Avance 500 spectrometer with an absolute frequency of 500.113 MHz at 300 K using $CDCl_3$ as the solvent. Chemical shifts were reported as parts per million from tetramethylsilane. The formation of a secondary ester link between fatty acids, indicating the formation of estolide, was verified with $^1$H NMR by a peak at about 4.84 ppm.

Estolide Number (EN):

The EN was measured by GC analysis. It should be understood that the EN of a composition specifically refers to EN characteristics of any estolide compounds present in the composition. Accordingly, an estolide composition having a particular EN may also comprise other components, such as natural or synthetic additives, other non-estolide base oils, fatty acid esters, e.g., triglycerides, and/or fatty acids, but the EN as used herein, unless otherwise indicated, refers to the value for the estolide fraction of the estolide composition.

Iodine Value (IV):

The iodine value is a measure of the degree of total unsaturation of an oil. IV is expressed in terms of centigrams of iodine absorbed per gram of oil sample. Therefore, the higher the iodine value of an oil the higher the level of unsaturation is of that oil. The IV may be measured and/or estimated by GC analysis. Where a composition includes unsaturated compounds other than estolides as set forth in Formula I, II, and III, the estolides can be separated from other unsaturated compounds present in the composition prior to measuring the iodine value of the constituent estolides. For example, if a composition includes unsaturated fatty acids or triglycerides comprising unsaturated fatty acids, these can be separated from the estolides present in the composition prior to measuring the iodine value for the one or more estolides.

Acid Value:

The acid value is a measure of the total acid present in an oil. Acid value may be determined by any suitable titration method known to those of ordinary skill in the art. For example, acid values may be determined by the amount of KOH that is required to neutralize a given sample of oil, and thus may be expressed in terms of mg KOH/g of oil.

Gas Chromatography (GC):

GC analysis was performed to evaluate the estolide number (EN) and iodine value (IV) of the estolides. This analysis was performed using an Agilent 6890N series gas chromatograph equipped with a flame-ionization detector and an autosampler/injector along with an SP-2380 30 m×0.25 mm i.d. column.

The parameters of the analysis were as follows: column flow at 1.0 mL/min with a helium head pressure of 14.99 psi; split ratio of 50:1; programmed ramp of 120-135° C. at 20° C./min, 135-265° C. at 7° C./min, hold for 5 min at 265° C.; injector and detector temperatures set at 250° C.

Measuring EN and IV by GC:

To perform these analyses, the fatty acid components of an estolide sample were reacted with MeOH to form fatty acid methyl esters by a method that left behind a hydroxy group at sites where estolide links were once present. Standards of fatty acid methyl esters were first analyzed to establish elution times.

Sample Preparation:

To prepare the samples, 10 mg of estolide was combined with 0.5 mL of 0.5M KOH/MeOH in a vial and heated at 100° C. for 1 hour. This was followed by the addition of 1.5 mL of 1.0 M $H_2SO_4$/MeOH and heated at 100° C. for 15 minutes and then allowed to cool to room temperature. One (1) mL of $H_2O$ and 1 mL of hexane were then added to the vial and the resulting liquid phases were mixed thoroughly. The layers were then allowed to phase separate for 1 minute. The bottom $H_2O$ layer was removed and discarded. A small amount of drying agent ($Na_2SO_4$ anhydrous) was then added to the organic layer after which the organic layer was then transferred to a 2 mL crimp cap vial and analyzed.

EN Calculation:

The EN is measured as the percent hydroxy fatty acids divided by the percent non-hydroxy fatty acids. As an example, a dimer estolide would result in half of the fatty acids containing a hydroxy functional group, with the other half lacking a hydroxyl functional group. Therefore, the EN would be 50% hydroxy fatty acids divided by 50% non-hydroxy fatty acids, resulting in an EN value of 1 that corresponds to the single estolide link between the capping fatty acid and base fatty acid of the dimer.

IV Calculation:

The iodine value is estimated by the following equation based on ASTM Method D97 (ASTM International, Conshohocken, Pa.):

$$IV = \sum 100 \times \frac{A_f \times MW_I \times db}{MW_f}$$

$A_f$=fraction of fatty compound in the sample
$MW_I$=253.81, atomic weight of two iodine atoms added to a double bond
db=number of double bonds on the fatty compound
$MW_f$=molecular weight of the fatty compound The properties of exemplary estolide compounds and compositions described herein are identified in the following examples and tables.

Other Measurements:

Except as otherwise described, pour point is measured by ASTM Method D97-96a, cloud point is measured by ASTM Method D2500, viscosity/kinematic viscosity is measured by ASTM Method D445-97, viscosity index is measured by ASTM Method D2270-93 (Reapproved 1998), specific gravity is measured by ASTM Method D4052, flash point is measured by ASTM Method D92, evaporative loss is measured by ASTM Method D5800, vapor pressure is measured by ASTM Method D5191, and acute aqueous toxicity is measured by Organization of Economic Cooperation and Development (OECD) 203.

Example 1

The acid catalyst reaction was conducted in a 50 gallon Pfaudler RT-Series glass-lined reactor. Oleic acid (65 Kg, OL 700, Twin Rivers) was added to the reactor with 70% perchloric acid (992.3 mL, Aldrich Cat#244252) and heated to 60° C. in vacuo (10 torr abs) for 24 hrs while continuously being agitated. After 24 hours the vacuum was released. 2-Ethylhexanol (29.97 Kg) was then added to the reactor and the vacuum was restored. The reaction was allowed to continue under the same conditions (60° C., 10 torr abs) for 4 more hours. At which time, KOH (645.58 g) was dissolved in 90% ethanol/water (5000 mL, 90% EtOH by volume) and added to the reactor to quench the acid. The solution was then allowed to cool for approximately 30 minutes. The contents of the reactor were then pumped through a 1 micron (μ) filter into an accumulator to filter out the salts. Water was then added to the accumulator to wash the oil. The two liquid phases were thoroughly mixed together for approximately 1 hour. The solution was then allowed to phase separate for approximately 30 minutes. The water layer was drained and disposed of. The organic layer was again pumped through a 1μ filter back into the reactor. The reactor was heated to 60° C. in vacuo (10 torr abs) until all ethanol and water ceased to distill from solution. The reactor was then heated to 100° C. in vacuo (10 torr abs) and that temperature was maintained until the 2-ethylhexanol ceased to distill from solution. The remaining material was then distilled using a Myers 15 Centrifugal Distillation still at 200° C. under an absolute pressure of approximately 12 microns (0.012 torr) to remove all monoester material leaving behind estolides (Ex. 1). Certain data are reported below in Table 1.

Example 2

The acid catalyst reaction was conducted in a 50 gallon Pfaudler RT-Series glass-lined reactor. Oleic acid (50 Kg, OL 700, Twin Rivers) and whole cut coconut fatty acid (18.754 Kg, TRC 110, Twin Rivers) were added to the reactor with 70% perchloric acid (1145 mL, Aldrich Cat#244252) and heated to 60° C. in vacuo (10 torr abs) for 24 hrs while continuously being agitated. After 24 hours the vacuum was released. 2-Ethylhexanol (34.58 Kg) was then added to the reactor and the vacuum was restored. The reaction was allowed to continue under the same conditions (60° C., 10 torr abs) for 4 more hours. At which time, KOH (744.9 g) was dissolved in 90% ethanol/water (5000 mL, 90% EtOH by volume) and added to the reactor to quench the acid. The solution was then allowed to cool for approximately 30 minutes. The contents of the reactor were then pumped through a 1μ filter into an accumulator to filter out the salts. Water was then added to the accumulator to wash the oil. The two liquid phases were thoroughly mixed together for approximately 1 hour. The solution was then allowed to phase separate for approximately 30 minutes. The water layer was drained and disposed of. The organic layer was again pumped through a 1μ filter back into the reactor. The reactor was heated to 60° C. in vacuo (10 torr abs) until all ethanol and water ceased to distill from solution. The reactor was then heated to 100° C. in vacuo (10 torr abs) and that temperature was maintained until the 2-ethylhexanol ceased to distill from solution. The remaining material was then distilled using a Myers 15 Centrifugal Distillation still at 200° C. under an absolute pressure of approximately 12 microns (0.012 torr) to remove all monoester material leaving behind estolides (Ex. 2). Certain data are reported below in Table 2.

Example 3

The estolides produced in Example 1 (Ex. 1) were subjected to distillation conditions in a Myers 15 Centrifugal Distillation still at 300° C. under an absolute pressure of approximately 12 microns (0.012 torr). This resulted in a primary distillate having a lower EN average (Ex. 3A), and a distillation residue having a higher EN average (Ex. 3B). Certain data are reported below in Table 1.

TABLE 1

| Estolide Base Stock | EN | Pour Point (° C.) | Iodine Value (cg/g) |
|---|---|---|---|
| Ex. 3A | 1.35 | −32 | 31.5 |
| Ex. 1 | 2.34 | −40 | 22.4 |
| Ex. 3B | 4.43 | −40 | 13.8 |

Example 4

Estolides produced in Example 2 (Ex. 2) were subjected to distillation conditions in a Myers 15 Centrifugal Distillation still at 300° C. under an absolute pressure of approximately 12 microns (0.012 torr). This resulted in a primary distillate having a lower EN average (Ex. 4A), and a distillation residue having a higher EN average (Ex. 4B). Certain data are reported below in Table 2.

TABLE 2

| Estolide Base Stock | EN | Pour Point (° C.) | Iodine Value (cg/g) |
|---|---|---|---|
| Ex. 4A | 1.31 | −30 | 13.8 |
| Ex. 2 | 1.82 | −33 | 13.2 |
| Ex. 4B | 3.22 | −36 | 9.0 |

Example 5

Oleic acid (1 part) and coconut fatty acids (1 part) (1 equiv. total fatty acids) were agitated in a glass reactor at 200-300 rpm. To the reaction mixture was added methanesulfonic acid (0.25 equiv), and the reactor was heated to 60° C. under nitrogen for 24 hrs. The reactor was allowed to cool to 25-50° C., and the crude reaction mixture was washed with water, dried, and filtered to provide sulfonated estolides. The presence of a mesylate residue in the resulting estolide compounds was confirmed by $^1$H NMR with a peak at about 3.0 ppm.

Example 6

Oleic acid (1 part) and coconut fatty acids (1 part) (1 equiv. total fatty acids) were agitated in a glass reactor at 200-300 rpm. To the reaction mixture was added methanesulfonic acid (0.25 equiv), and the reactor was heated to 60° C. under nitrogen for 24 hrs. While holding at 60° C., a solution of NaOH (0.35 equiv) in 5 vol. % of water was slowly added to the reaction mixture. The resulting mixture was heated under nitrogen at 80-100° C. for about 2 hrs. Acetic acid (0.25 equiv) was then added to the reactor, and the mixture was allowed to cool to 25-50° C. The crude reaction mixture was washed with water until the final aqueous wash had a final pH of 3.0-7.0. During each wash, the mixture was agitated for 30-60 minutes, and the aqueous bottom layer was drained and set aside. Acetic acid (1-5 wt. % of fatty acids) was added when necessary to clear any emulsions or adjust pH. A sample of the washed reaction mixture was analyzed and the elimination of mesylate residues was confirmed by $^1$H NMR with the absence of a peak at about 3.0 ppm.

To the washed reaction mixture was added 2-ethylhexanol (1.25 equiv) and methanesulfonic acid (0.025 equiv). Under distillation conditions and reduced pressure (10-100 mbar), the reaction mixture was heated to 60° C. and agitated for 2 hrs, and the primary distillate was collected (water and small amounts of 2-ethylhexanol). The reactor was then cooled to ambient temperature and washed with water until the pH of the final aqueous solution reaches 5.0-7.0. During each wash, the mixture was agitated for 30-60 minutes, the layers were separated, and the aqueous bottom layer was drained and set aside. Acetic acid was added when necessary to facilitate separation. The washed organic layer was then subjected to further distillation conditions to remove any remaining water and unreacted 2-ethylhexanol to provide demesylated, esterified estolides.

Example 7

Oleic acid (1 equiv.) was agitated in a glass reactor at 200-300 rpm. To the reaction mixture was added sulfuric acid (0.25 equiv), and the reactor was heated to 55° C. under nitrogen for 24 hrs. The reactor was allowed to cool to 25-50° C., and a small portion of the crude reaction mixture was washed with water, dried, and filtered to provide sulfated oleic estolides. The presence of a sulfate residue in the resulting crude reaction mixture was confirmed by $^1$H NMR with a peak at about 4.7 ppm. The resulting crude reaction mixture was treated with 50% sodium hydroxide (2.2-2.4 equiv.) at 100° C. for 2-18 hours. The crude reaction mixture was neutralized with acetic acid followed by washing with water and dried under vacuum. The resulting estolide product was analyzed and the elimination of sulfate residues was confirmed by $^1$H NMR with the absence of a peak at about 4.7 ppm.

Example 8

Oleic acid (1.0 kg, Acme Hardesty) was agitated in a glass reactor at 200-300 rpm. To the reaction mixture was added methanesulfonic acid (0.50 equiv), and the reactor was heated to 60° C. under nitrogen for 24 hours. A sample of the crude reaction mixture was analyzed by $^1$H NMR to confirm the presence of the mesylate signal at about 3.0 ppm. The reactor was allowed to cool to 25-40° C. and the crude reaction mixture was washed with water until the final aqueous wash had a final pH of 3.0-7.0. During each wash, the mixture was agitated for 30-60 minutes, the layers were separated, and the aqueous bottom layer was drained and set aside.

To the washed estolide free acid mixture was added 2-ethylhexanol (2.0 equiv) and methanesulfonic acid methanesulfonic acid (0.025 eq). Under distillation conditions and reduced pressure (10-100 mbar), the reaction mixture was heated to 80° C. and agitated for 2 hours, and the primary distillate was collected (water and small amounts of 2-ethylhexanol). The reactor was then cooled to ambient temperature and washed with water until the pH of the final aqueous solution reaches 5.0-7.0. During each wash, the mixture was agitated for 30-60 minutes, the layers were separated, and the aqueous bottom layer was drained and set aside. The estolide ester mixture was placed under vacuum at 50° C. to remove traces of water. Analysis of the estolide ester mixture by $^1$H NMR confirmed the presence of the mesylate at 3.0 ppm.

The resulting estolide ester mixture was treated with pyridine (0.5-4.0 equiv.) and heated to 110° C. for 3-24 hours under nitrogen. A sample of the reaction mixture was analyzed by $^1$H NMR and the mesylate signal at 3.0 ppm was absent. The reaction mixture was subjected to distillation conditions to remove residual pyridine and any unreacted 2-ethylhexanol to provide demesylated, esterified estolides.

Example 9

Two batches of sulfonated estolides were prepared separately. The first batch was prepared by agitating coconut fatty acids (20 g), oleic acid (30 g), and methanesulfonic acid (19.5 g) at 60° C. for 1-3 hrs in a glass reactor. The second batch was prepared by agitating coconut fatty acids (30 g), oleic acid (20 g), and methanesulfonic acid (20.6 g) at 60° C. for 1-3 hrs in a glass reactor. The two reaction mixtures were washed with water to remove excess methanesulfonic acid, and combined to provide a crude estolide reaction product. $^1$H NMR analysis of the crude reaction product indicated the presence of mesylated estolides.

The crude estolide reaction product (94 g) was charged to a 250 mL round bottom flask and a short path distillation head was attached to the flask. The setup was connected to a vacuum pump protected by a dry ice trap. The system was put under a vacuum of about 0.5 torr abs. The temperature was slowly raised from 25° C. to 142° C. over 3 hrs. The temperature was then maintained in the range 142° C. to 145° C. for about 30 mins. About 30 g of distillate was collected in the receiver.

$^1$H NMR analysis of the purified residue contained in the round bottom flask detected the presence of the desired estolide product, without the presence of methanesulfonic acid or mesylated estolides. $^1$H NMR of the distillate detected unreacted coconut and oleic fatty acids, as well as methanesulfonic acid generated from the elimination of the mesylate.

Example 10

Oleic acid (283 g) was fed over 1 hr by syringe pump to a solution of coconut fatty acids (426 g) and methanesulfonic acid (292 g) at 60° C. The reaction mixture was heated for an additional 20 mins, and then cooled to ambient temperature. The reaction mixture was then washed twice with 300 g water and once with 140 g brine to remove excess methanesulfonic acid, providing a crude estolide reaction product. The crude reaction product was heated to 100° C. at 2 torr abs and about 15 g of aqueous distillate was collected.

The purified residue was then sent through a wiped film evaporator. The temperature of the bath connected to the jacket was 170° C. and the temperature of the cold finger was 70° C. The vacuum on the system was about 0.3 torr abs. After about 2 hrs, the purified residue was processed through the wiped film evaporator. After processing through the wiped film evaporator, $^1$H NMR of the resulting product detected the presence of mesylated estolides.

Example 11

Oleic acid (353 g) was added over 1 hr to a solution of coconut fatty acids (530 g) and methanesulfonic acid (726.6 g) at 60° C. The reaction mixture was heated for an additional 20 mins, and then cooled to ambient temperature. The reaction mixture was then washed twice with about 390 g water and then once with 130 g brine to remove excess methanesulfonic acid, providing a crude estolide reaction product. The crude reaction product was transferred to a flask equipped with a short path distillation head. The crude reaction product was heated to 160° C. under a vacuum of 2 torr abs, and the temperature was maintained for 1 hr. About 12 g of aqueous distillate collected during the heating ramp to 160° C.

The purified residue was then sent through the wiped film evaporator. The jacket bath was set at 220° C., the cold finger bath was set at 70° C., and the vacuum was about 0.7 torr abs. After about 1 hr 20 mins, the purified residue was processed through the wiped film evaporator. After processing through the wiped film evaporator, $^1$H NMR analysis of the resulting product detected the presence of the desired estolide product, without the presence of methanesulfonic acid or mesylated estolides.

Example 12

Oleic acid (353 g) was fed by syringe pump over 1 hr to a solution of coconut fatty acids (531 g) and methanesulfonic acid (363 g) at 60° C. The solution was heated an additional hour at 60° C. After cooling the reaction mixture was washed twice with 380 g water to remove excess methanesulfonic acid, providing a crude estolide reaction product. The crude reaction product was charged to a flask equipped with a short path distillation head connected to a vacuum pump. The crude reaction product was heated for 1 hr at 160° C. under a vacuum of 8 torr abs. During the temperature ramp to 160° C., about 26 g of aqueous distillate collected.

The purified residue was then sent through a wipe film over 3.5 hours. The jacket bath was set at 240° C., the cold finger bath was set at 45° C., and the vacuum was about 0.6 torr abs. After processing through the wiped film evaporator, $^1$H NMR analysis of the resulting product detected the presence of the desired estolide product, without the presence of methanesulfonic acid or mesylated estolides.

Example 13

Oleic acid (320 g), coconut fatty acids (881 g), and methanesulfonic acid (494 g) were stirred with a mechanical stirrer at 60-65° C. for 1 hr. After cooling the reaction mixture was washed three times with about 525 g water to remove excess methanesulfonic acid, providing a crude estolide reaction product. The crude reaction product was then transferred to a flask equipped with a mechanical stirrer and heated at 160° C. for 1 hr under a vacuum of 25 to 33 torr abs. During the temperature ramp to 160° C., about 26.3 g of aqueous distillate was collected. The purified residue was then sent through the wiped film evaporator. The temperature of the jacket bath was 210° C., the temperature of the cold finger bath was 40° C., and the vacuum was about 0.4 torr abs. After processing through the wiped film evaporator, $^1$H NMR analysis of the resulting product detected the presence of the desired estolide product, without the presence of methanesulfonic acid or mesylated estolides.

The invention claimed is:

1. A process of producing an estolide base oil comprising providing at least one first estolide compound having at least one sulfonate residue; and
   eliminating the at least one sulfonate residue by exposing the at least one first estolide compound to heat and/or basic conditions to provide at least one desulfonated estolide compound that is unsaturated at the site of elimination.

2. The process according to claim 1, wherein the at least one first estolide compound is prepared by a process that includes oligomerizing at least one first fatty acid reactant having at least one site of unsaturation with at least one second fatty acid reactant in the presence of a sulfonic acid catalyst.

3. The process according to claim 2, wherein the at least one first fatty acid reactant is selected from one or more of an unsaturated fatty acid, an unsaturated fatty acid ester, or an unsaturated fatty acid oligomer.

4. The process according to claim 2, wherein the at least one second fatty acid reactant is selected from one or more of a saturated fatty acid or an unsaturated fatty acid.

5. The process according to claim 2, wherein the sulfonic acid catalyst is an unsubstituted alkyl sulfonic acid.

6. The process according to claim 2, wherein at least a portion of the oligomerizing occurs at a temperature of 100° C. or less.

7. The process according to claim 6, wherein at least a portion of the oligomerizing occurs at a temperature 70° C. or less.

8. The process according to claim 6, wherein at least a portion of the oligomerizing occurs within a temperature range of 25° C. to 75° C.

9. The process according to claim 8, wherein at least a portion of the oligomerizing occurs within a temperature range of 15° C. to 60° C.

10. The process according to claim 8, wherein at least a portion of the oligomerizing occurs at a pressure of 1 atm or more.

11. The process according to claim 1, wherein eliminating said at least one sulfonate residue includes contacting the at least one first estolide compound with a base.

12. The process according to claim 11, wherein the base comprises at least one metal hydroxide.

13. The process according to claim 12, wherein the base is selected from sodium hydroxide and potassium hydroxide.

14. The process according to claim 1, wherein eliminating said at least one sulfonate residue includes heating the at least one first estolide compound to a temperature of at least 100° C.

15. The process according to claim 1, wherein eliminating said at least one sulfonate residue includes heating the at least one first estolide compound to a temperature of at least 140° C.

16. The process according to claim 14, wherein eliminating said at least one sulfonate residue includes heating the at least one first estolide compound under reduced pressure that is less than 1 atm abs.

17. The process according to claim 16, wherein the reduced pressure is 25 torr abs or less.

18. The process according to claim 1, further comprising esterifying the at least one desulfonated estolide compound with at least one alcohol to provide at least one esterified estolide compound.

19. The process according to claim 18, further comprising hydrogenating the at least one esterified estolide compound to provide at least one saturated estolide compound.

20. The process according to claim 1, wherein the at least one first estolide compound is selected from compounds of Formula III:

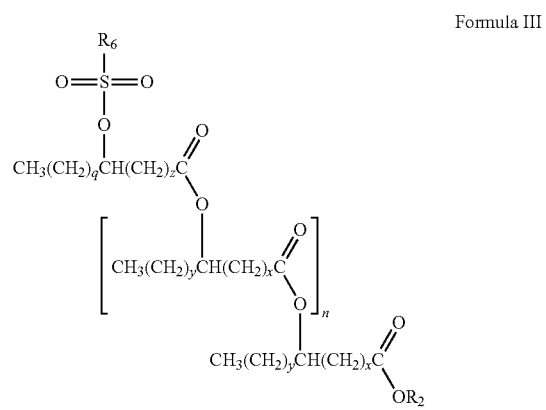

Formula III wherein
$R_6$ is selected from —OH, optionally substituted alkyl, and optionally substituted aryl;
z is an integer selected from 0 to 12;
q is an integer selected from 0 to 10;
x is, independently for each occurrence, an integer selected from 0 to 10;
y is, independently for each occurrence, an integer selected from 0 to 10;
n is an integer selected from 0 to 20; and
$R_2$ is selected from hydrogen and optionally substituted alkyl that is saturated or unsaturated, and branched or unbranched,
wherein each fatty acid chain residue is unsubstituted.

21. The process according to claim 20, wherein z is an integer selected from 7 and 8.

22. The process according to claim 20, wherein q is an integer selected from 7 and 8.

23. The process according to claim 20, wherein n is an integer selected from 0 to 12.

24. The process according to claim 20, wherein n is an integer selected from 1 to 20.

25. The process according to claim 20, wherein x+y is, independently for each fatty acid chain residue, an integer selected from 13 to 15.

26. The process according to claim 20, wherein $R_6$ is —OH.

27. The process according to claim 11, wherein the base is a carboxylate salt.

28. The process according to claim 11, wherein the base is a nitrogenous base.

29. The process according to claim 28, wherein the base is selected from one or more of a tertiary amine or an aromatic amine.

30. The process according to claim 20, wherein $R_6$ is an optionally substituted alkyl.

31. The process according to claim 30, wherein $R_6$ is unsubstituted.

32. The process according to claim 20, wherein $R_6$ is an optionally substituted aryl.

33. The process according to claim 2, wherein the sulfonic acid catalyst is an optionally substituted aryl sulfonic acid.

34. The process according to claim 2, wherein the sulfonic acid catalyst is sulfuric acid.

* * * * *